United States Patent [19]
Lebron et al.

[11] Patent Number: 5,041,973
[45] Date of Patent: Aug. 20, 1991

[54] CARDIAC MAPPING SYSTEM SIMULATOR

[75] Inventors: Fernando C. Lebron; Jonathan P. Brown, both of London, Canada

[73] Assignee: London Health Association, London, Canada

[21] Appl. No.: 345,979

[22] Filed: May 1, 1989

[30] Foreign Application Priority Data

Oct. 25, 1988 [CA] Canada ................................. 581125

[51] Int. Cl.[5] .............................................. G06F 15/42
[52] U.S. Cl. ........................... 364/413.05; 364/413.02; 128/642; 434/272
[58] Field of Search ...................... 364/413.02, 413.05, 364/578; 128/642; 434/272

[56] References Cited

U.S. PATENT DOCUMENTS

| | | |
|---|---|---|
| 3,323,068 | 5/1967 | Woods . |
| 3,453,745 | 7/1969 | Spivack . |
| 3,459,115 | 9/1969 | Partridge . |
| 3,797,129 | 3/1974 | Ravin et al. . |
| 4,091,549 | 5/1978 | Driller et al. . |
| 4,204,261 | 5/1980 | Ruszala et al. . |
| 4,205,386 | 5/1980 | Ruszala et al. . |
| 4,293,916 | 10/1981 | Del Re et al. ........................ 364/571 |
| 4,352,163 | 9/1982 | Schultz, Jr. et al. . |
| 4,415,818 | 11/1983 | Ogawa et al. ........................ 307/465 |
| 4,503,858 | 3/1985 | Markowitz et al. . |
| 4,639,223 | 1/1987 | Keller, Jr. . |
| 4,676,253 | 6/1987 | Newman et al. . |
| 4,699,147 | 9/1987 | Chilson et al. ........................ 128/642 |
| 4,736,322 | 4/1988 | Clifford ........................ 364/413.01 |
| 4,906,983 | 3/1990 | Parker ........................ 340/747 |

OTHER PUBLICATIONS

Schulz et al., "A Precision Pump for Simulated Cardiographic Studies," J. Nucl. Med. 22:643–644, 1981.

Primary Examiner—Jerry Smith
Assistant Examiner—Russell Cass
Attorney, Agent, or Firm—Bell, Seltzer, Park & Gibson

[57] ABSTRACT

A cardiac mapping system simulator comprising a microprocessor for simulating the electrical signal propagation of a heartbeat as it moves across the surface of a heart. A series of impulses that mimic the electrophysiological waveform are generated forming a two-dimensional map depicting heart activity. The series of pulses are generated in accordance with predetermined patterns and applied to the inputs of a cardiac mapping system or electrophysiology (E.P.) lab equipment in order to assess the operating condition of the cardiac mapping system or E.P. lab equipment prior to use on patients.

18 Claims, 5 Drawing Sheets

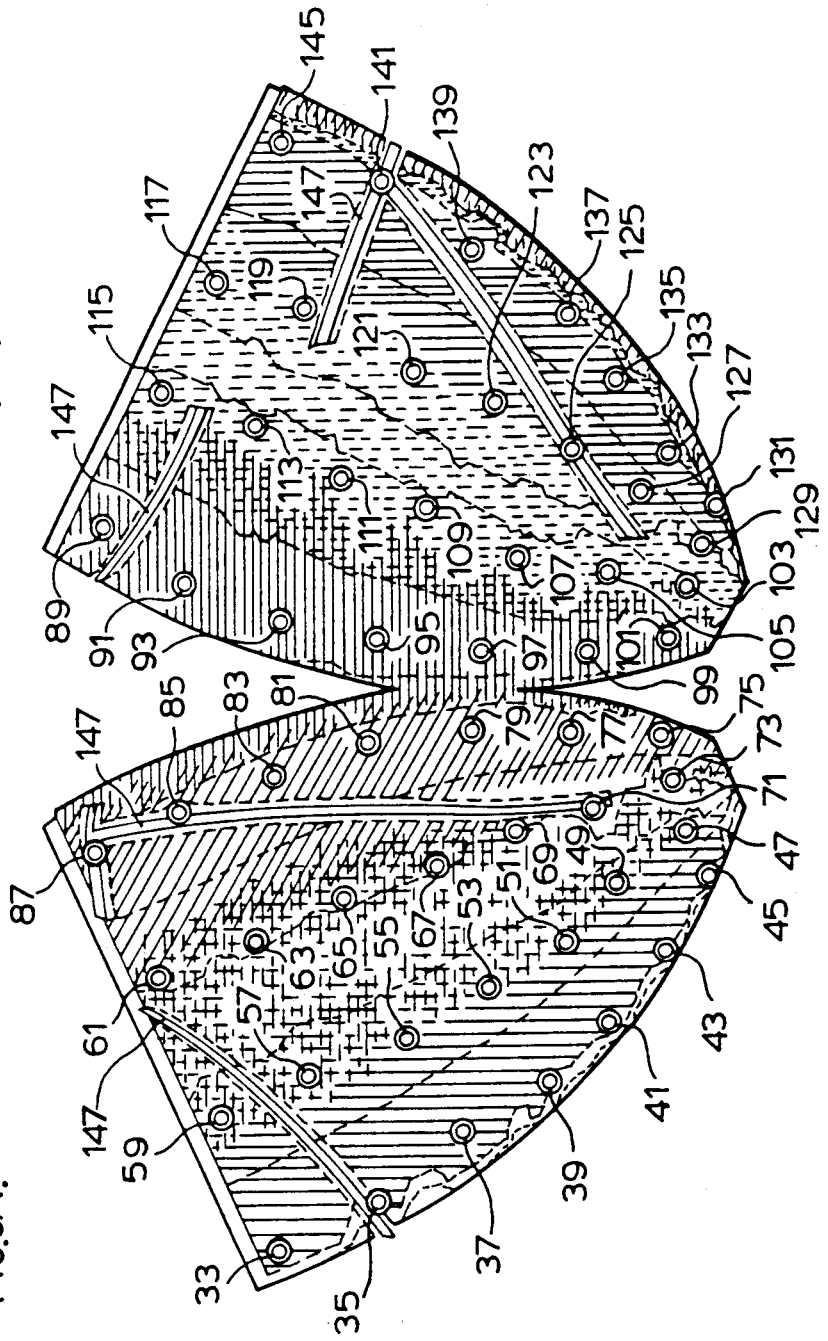

CARDIAC MAPPING SYSTEM SIMULATOR

FIELD OF THE INVENTION

The present invention relates in general to electrical signal generating systems and more particularly to a cardiac mapping system simulator for generating a series of signals which simulate two-dimensional electrophysiological impulses.

BACKGROUND OF THE INVENTION

Medical analysis of the heart muscle has revealed that each normal heart contraction originates from an area in the upper right atrium called the sinus auricular node, and spreads in the form of a depolarization wave through the atrioventricular node, across the heart to the ventricular myocardium. The depolarization wave then spreads through the muscular tissue of the ventricle to cause the ventricle to contract for pumping blood through the arteries.

Thus, although normal contraction of the heart is referred to in common parlance as being a "heartbeat", in actuality the contraction proceeds as a wave which travels across the surface of the heart. In the event that various cells within the heart tissue have been damaged, propagation of the depolarization wave across the heart may be obstructed. Furthermore, in the event that the cells in a specific region of the heart have been damaged, conflicting depolarization waves may be generated by the affected cells which interfere with the normal heart rhythm, a condition known as cardiac arrhythmia.

The surgical treatment of cardiac arrhythmias has been facilitated by an understanding of the mechanisms of arrhythmia gained through a precise description of the structure and function of the cardiac tissues. To this end, advances in medical technology have resulted in development of various devices for investigating electrical activity, and thereby interoperatively identifying the sources of cardiac arrhythmias within a patient.

One such developmental tool is known as a cardiac mapping system comprising an electrode array having a plurality of electrodes arranged in a three-dimensional grid, a plurality of preamplifier units for amplifying signals received from the electrode array, a data acquisition sub-system for performing analog-to-digital conversion of the signals received from the preamplifier units, and an analysis and display processor for displaying individual epicardial waveforms as they propagate across the heart during each contraction.

In operation, the chest cavity of a patient is opened and the electrode array is located over or within the heart muscle. The electrodes detect bioelectric phenomena of the heart muscle at their individual locations across the surface of the heart and in response generate corresponding analog-electrical impulses representative thereof. The analysis and display processor captures and processes the data received from the acquisition sub-system and displays the individual waveforms. The information is typically displayed on a colour monitor as well as remote monitors in the operating room in the form of an isochronal map. Preferably, the data from the electrodes are then stored on an optical disc or other suitable storage apparatus.

It is important that proper functioning of the cardiac mapping system be assessed prior to use on patients since interpretation of results in the operating theatre will determine the diagnosis and hence the procedure to be performed.

A number of prior art systems have been developed for generating signals which simulate various electrophysiological impulses. For example, U.S. Pat. No. 3,323,068 (Woods) discloses an electrocardiogram simulator for generating EKG waveforms of the human heart. The simulator according to this prior art patent generates a single pulse conforming to a standard idealized EKG wave in order to set up or trouble shoot EKG analysis equipment.

Similarly, U.S. Pat. No. 3,469,115 (Cartridge) discloses a cardiac waveform simulator for generating a pulse having a generally triangular shape and a rise time to fall time characteristic closely resembling the pulses of a human cardiac waveform.

U.S. Pat. No. 4,204,261 (Ruszala et al) teaches a complex analog signal generator for generating a complete complex waveform which is divided into a plurality of outputs for testing and calibrating various types of medical equipment such as electrocardiogram displays and blood pressure waveform displays. Related U.S. Pat. No. 4,205,386 (Ruszala et al) teaches an electrocardiographic and blood pressure waveform simulator device for simulating both electrocardiographic and blood pressure waveforms, with the beginning of the blood pressure waveform being delayed from the beginning of the electrocardiographic waveform so that the waves are provided in a time sequence corresponding to waveforms that would ordinarily be supplied by a live patient.

U.S. Pat. No. 4,352,163 (Schultz et al) discloses a vector-cardiogram simulator for generating three distinct waveforms for simulating electrical activity within the human heart along three separate axes. The three generated waveforms are applied to the input of a vector-cardiogram machine for the purpose of calibration and testing.

The above discussed prior art patents all relate to systems for generating analog signals representative of electrophysiological activity in a single dimension with respect to time. A typical display output for such prior art systems would be in the form of a graph depicting electrical amplitude on one axis versus time on the other axis. Thus, such prior art systems provide signals which simulate the electrophysiological characteristics of a heartbeat, but do not provide for simulation of electrophysiological waves in two dimensions with respect to time (i.e. a simulation of the depolarization wave which travels across the heart surface).

SUMMARY OF THE INVENTION

According to the present invention, apparatus is provided for generating a series of signals for simulating two-dimensional electrophysiological impulses. The generated signals appear on outputs of the apparatus which are arranged to form a two-dimensional array or grid conforming to the grid pattern of the electrode array used in the cardiac mapping system. The apparatus preferably includes microprocessor circuitry for generating signals of sufficient complexity in two dimensions to enable thorough testing of the cardiac mapping system. Other arrays may be configured as global, patching or bands for either the epicardial or endocardial surfaces.

It is typically necessary to generate a variety of maps in order to completely characterize the system and ensure correct functioning of each channel corresponding to a grid on the electrode array. Thus, the microprocessor circuitry allows for flexible programming to generate the various complex signal patterns corresponding to the isochronal maps. The patterns which are generated by the simulator preferably include vertical, horizontal and square isochronal maps.

It is believed that no cardiac mapping simulator has hitherto been developed for generating waveforms in the form of timed sequences of signals for simulating two-dimensional electrophysiological impulses.

According to the present invention, there is provided an apparatus for generating a two-dimensional pattern of timed simulated electrophysiological impulses for application to an electrophysiological impulse display device, comprising programmable circuitry for generating a succession of digital signals, a circuit for receiving the aforementioned succession of digital signals and in response generating a succession of output signals on predetermined outputs thereof, wherein the outputs are arranged to form a two-dimensional array, and circuitry for shaping the output signals to resemble electrophysiological impulses, whereby the succession of output signals forms a two-dimensional pattern of simulated electrophysiological impulses for application to the display device.

BRIEF DESCRIPTION OF THE DRAWINGS

The present invention will be described in greater detail below in conjunction with the following drawings, in which:

FIGS. 3A and 3B are anterior and posterior views of an output map of the cardiac mapping system showing a vertical test map.

DETAILED DESCRIPTION OF THE PREFERRED EMBODIMENTS

Figure 1:
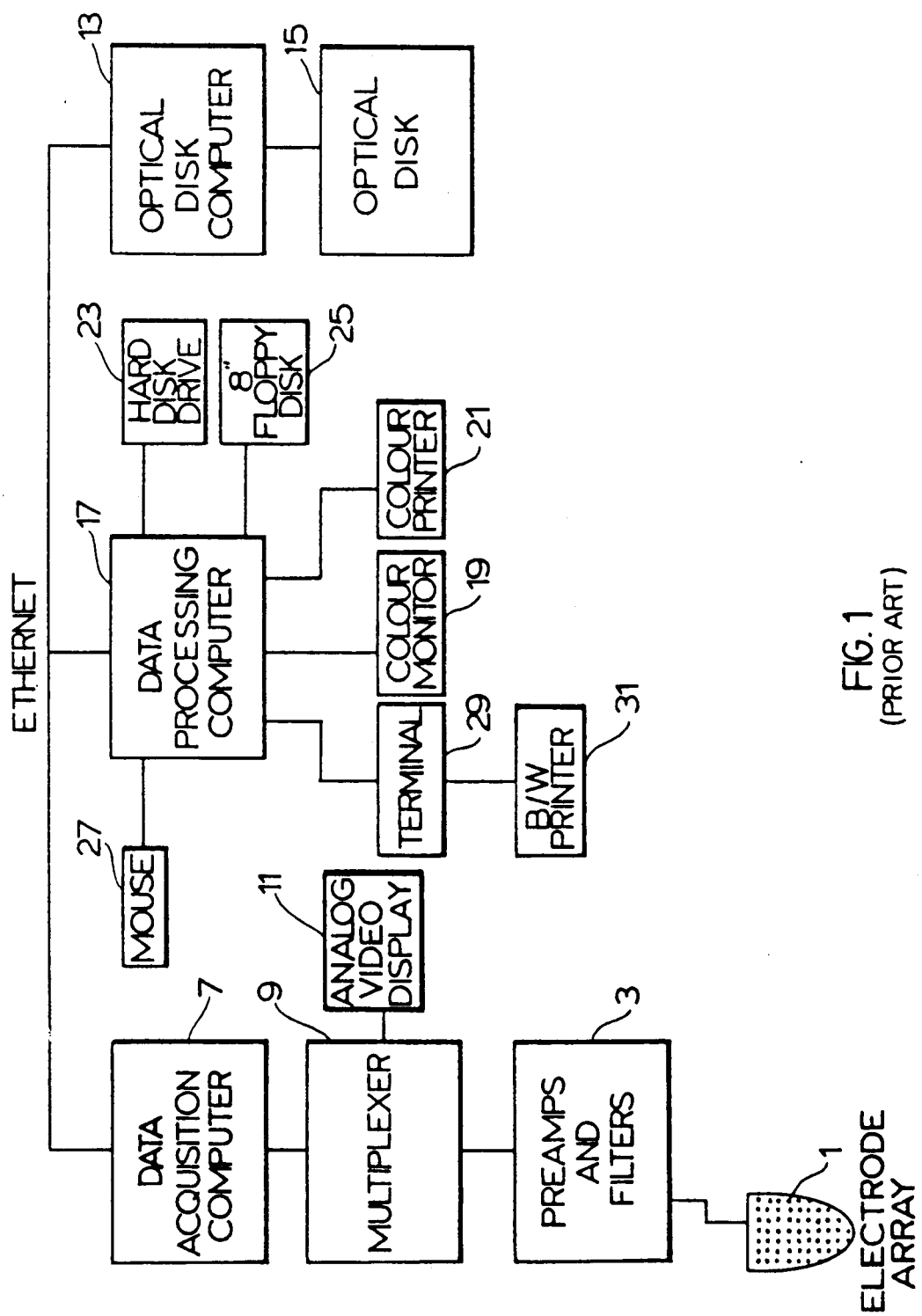
FIG. 1 is a block diagram of a cardiac mapping system.

Turning to FIG. 1, a cardiac mapping system is shown in block diagram format comprised of an electrode array 1 incorporating a plurality of electrodes for detecting electrophysiological impulses and in response generating and transmitting analog impulse signals to preamplifier and filter circuitry 3. The preamplifier and filter circuitry 3 is typically located under the operating room table. The electrode array 1 is attached to a human (or animal) heart 5 in the manner shown with reference to FIG. 2. A bundle of wires extends from the individual electrodes of the electrode array to a connector of the preamplifier and filter circuitry 3. Analog signal outputs from the preamplifier and filter circuitry 3 are transmitted to a data acquisition computer 7 by means of a multiplexer 9. An analog display 11 is connected to the multiplexer 9 for generating an analog display of a pre-selected one or more of the multiplexed signals received from the preamplifier and filter circuitry 3.

The data acquisition computer 7 performs an analog-to-digital transformation of the signals received from multiplexer 9, and the digital data is transmitted for storage to an optical disc computer 13 and associated optical disc storage medium 15. The data from the electrodes is sampled by the optical disc computer at a rate of preferably 1,000 Hz per electrode with 12-bit resolution.

The digital data signals generated by the data acquisition computer 7 are also applied to a data processing computer 17 which captures a preferably 10-second segment of the data signals and in response displays individual epicardial waveforms.

The processed data from computer 17 can then be displayed on a colour monitor 19 as well as remote monitors in the operating room and at the location of the acquisition sub-system (e.g. via analog display 11). Upon capturing the data, an operator at the data processing computer 17 can review the individual waveforms or request a complete isochronal map as shown in FIG. 3. The map is displayed on the colour monitor 19 as well as being transferred to a colour ink-jet printer 21.

The data processing computer 17 is also typically provided with well known peripherals such as hard disc drive 23, floppy disc drive 25, mouse 27, terminal 29 and black-and-white printer 31.

Turning to FIGS. 3A and 3B, a typical isochronal map is shown as it would appear on colour monitor 19 and colour printer 21 with the exception that the graph of FIG. 3 is in black and white instead of colour. FIG. 3A represents the anterior view of the electrode array 1, while FIG. 3B represents a posterior view. The electrode array 1 is comprised of a plurality of spaced apart electrodes (e.g. from as few as 5 to as many as 265, or more). However, according to the embodiment illustrated, 56 epicardial electrodes 33-145 are arranged in seven rows by eight columns across the surface of the array 5, for detecting electrophysiological impulses at the heart's surface.

Time durations from a predetermined one of the electrodes, chosen as a "Reference electrode", are measured to each of the other electrodes. These activation times are plotted on an outline of the heart and common activation times are connected in order to form isochronal lines (i.e. the lines of vertical shading in FIGS. 3A and 3B which correspond to respective colours in a colour isochronal map).

Solid black lines 147 indicate anatomical landmarks in the heart (e.g. coronary arteries).

Figure 2:
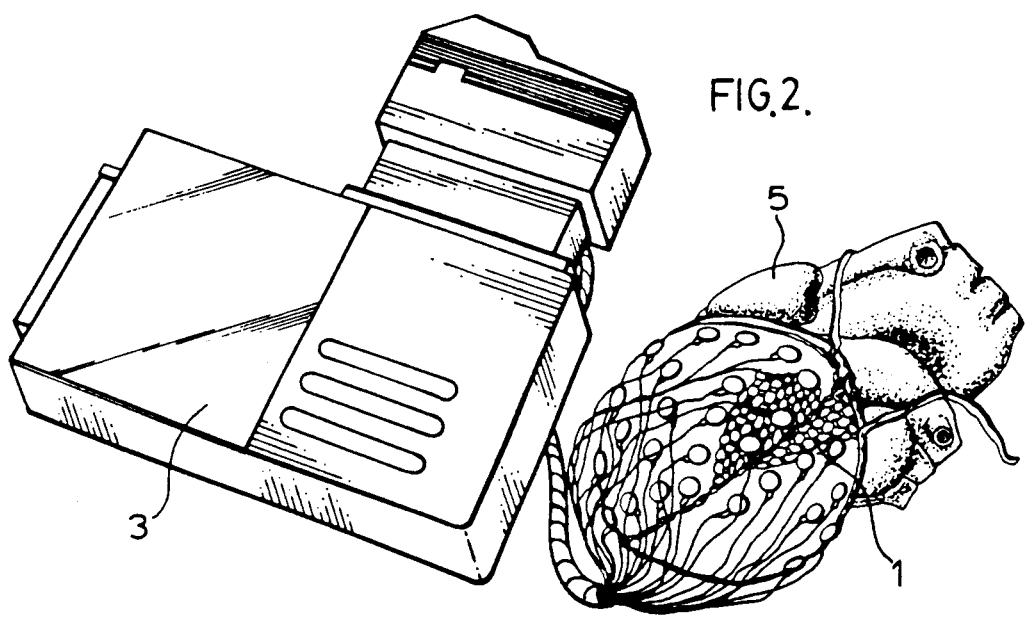
FIG. 2 is a perspective view of a cardiac mapping system electrode array mounted on a heart model and connected to an input portion of the cardiac mapping system.
Figure 4:
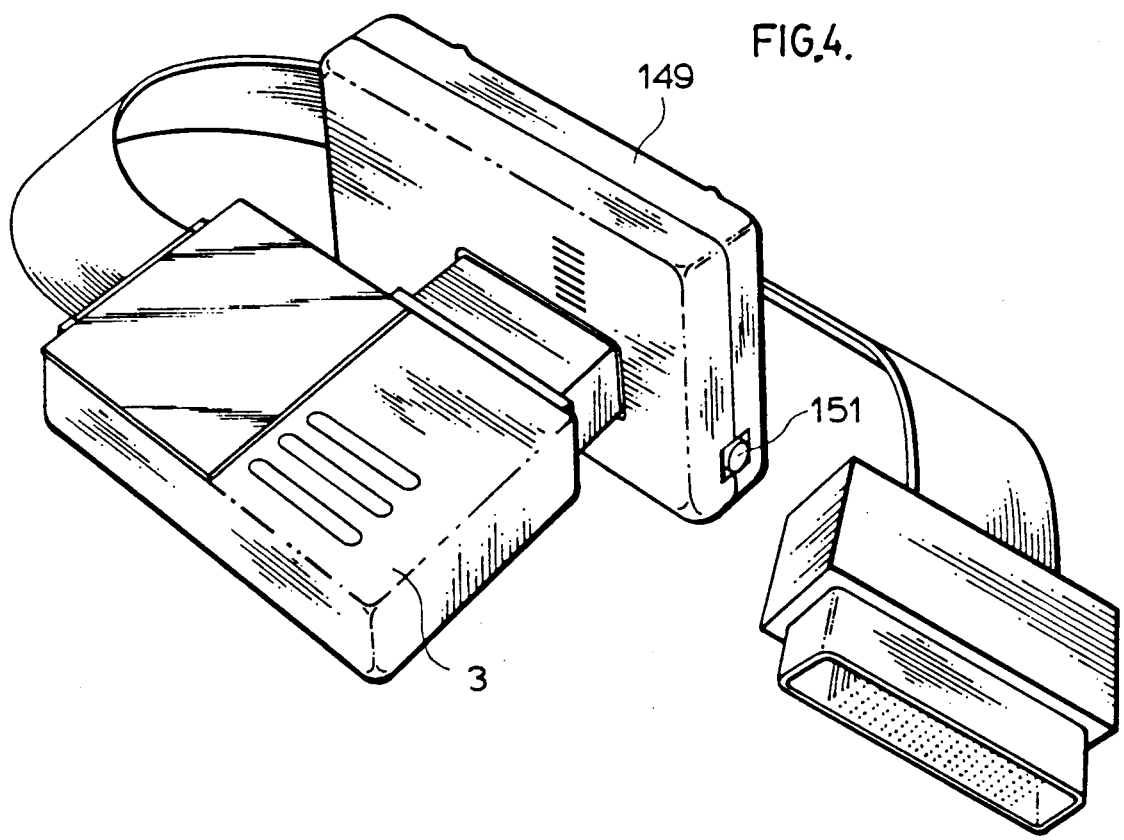
FIG. 4 is a perspective view of the cardiac mapping system simulator of the present invention connected to the input portion of the cardiac mapping system.

FIG. 4 shows the cardiac mapping simulator 149 of the present invention connected to the preamplifier and filter circuitry 3 discussed with reference to FIGS. 1 and 2. The simulator 149 is provided with a start switch 151 for initiating simulation of two-dimensional electrophysiological impulses which are used to test the cardiac mapping system.

Figure 5A:
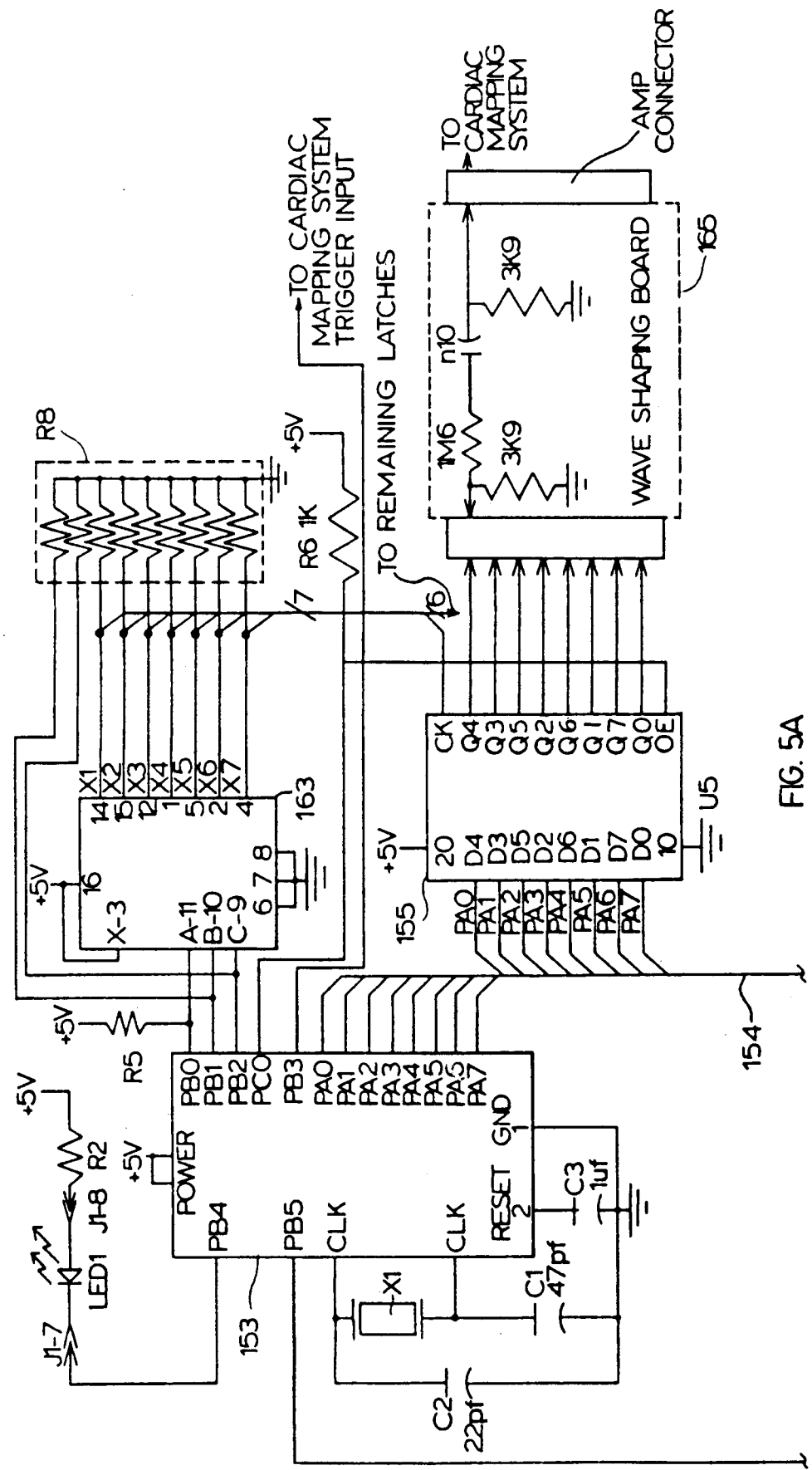
FIGS. 5A and 5B are a schematic diagram of the cardiac mapping system simulator according to a preferred embodiment of the present invention.
Figure 5B:
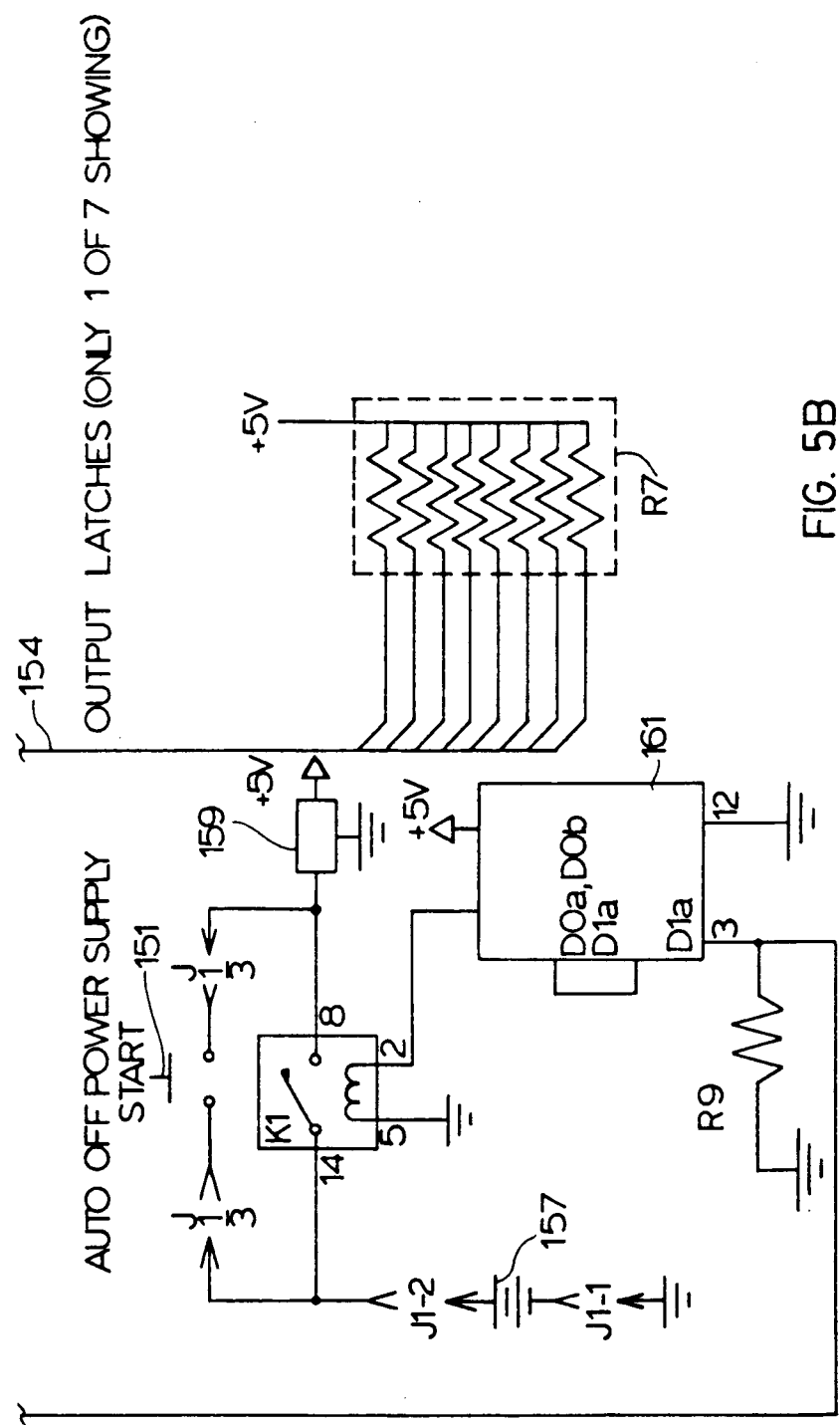

As shown in greater detail with reference to FIGS. 5A and 5B, the cardiac mapping system simulator incorporates a microprocessor 153 for generating a succession of digital signals according to a known pattern via outputs PA0-PA7 via data bus 154 to successive inputs of a plurality of (e.g. seven) output latches. For the purpose of illustration, only one of the output latches 155 is illustrated. Although not shown, the remaining six output latches are connected to data ports PA0--PA7 of microprocessor 153 via bus 154 in a manner identical to that shown with reference to output latch 155.

The microprocessor 153 is preferably a single-chip computer such as the Motorola MC68705R3S integrated HMOS microprocessor featuring on-board RAM, EPROM, bi-directional input/output lines, etc. An external crystal Xl is connected to the microprocessor for generating a system clock frequency of preferably 1 MHz resulting in an instruction cycle time of 4 microseconds.

The clock frequency is dictated by the crystal's resonating frequency. Capacitors C1 and C2 are coupling capacitors, while C3 provides a reset-delay at power ON. An LEDI may optionally be connected via terminals J1-7 and J1-8 to an input/output port PB4 of microprocessor 153 and via current limiting resistor R2 to the +5 volt power source for indicating when the simulator is activated.

The microprocessor 153, output latch 155 and other circuitry of the simulator is powered by means of a 9-volt battery 157 connected at terminals J1-1 and J1-2 to start switch 151, relay K1 and regulator 159 for generating a regulated 5-volt DC output to the various electronic components of the simulator.

Depression of the start switch 151 results in power being momentarily applied to power the microprocessor 153, thereby implementing an initialization routine. The initialization routine of microprocessor 153 causes a high-to-low logic transition on output PB5. This causes the $\overline{Q0a}$ output of a flip-flop 161 to go to a logic high level, thereby energizing the relay coil of relay K1 for closing the relay contact and providing battery supply to the system. Three sections of the flip-flop 161 are connected in parallel to supply the current required by relay K1. The initialization routine also outputs a 100 msec pulse to trigger the cardiac mapping system via an output port PB3.

At the end of the map generation routines (discussed in greater detail below), the microprocessor 153 causes the PB5 output to go to a logic high level, thereby causing the $\overline{Q0a}$ output of flip-flop 161 to return to a logic low level, for opening the relay contact and disconnecting power from the system.

Thus, according to the circuit of the present invention, the mapping simulator does not consume any energy from battery 157 when it is not in use, thereby prolonging the operating life of the battery.

Input/output lines PB0-PB2 of microprocessor 153 are arranged as BCD (Binary Coded Decimal) outputs for driving a one-of-eight decoder 163. The X1-X7 outputs of decoder 163 are connected to respective clock inputs CK of the seven output latches. The X1-X7 outputs of decoder 163 are active high and are used to select individual ones of the output latches to receive data from microprocessor 153 via the respective D0-D7 inputs.

The data bus 154 connecting outputs PA0-PA7 of microprocessor 153 to respective data inputs D0-D7 of the seven output latches is also connected via a resistor array R7 to the +5-volt power source for ensuring proper tri-state impedance conditions when microprocessor 153 is not generating data for output via the PA0-PA7 terminals. Similarly, respective outputs X1-X7 of decoder 163 as well as outputs PB1 and PB2 of microprocessor 153 are connected to ground via a further resistor array R8, while output PB0 is connected to the logic high power source +5-volt via resistor R5.

Resistor arrays R7 and R8 are preferably disposed within a single in-line package (SIP).

As indicated above, seven 8-bit output latches are provided for generating simulated electrophysiological signals corresponding to respective ones of the 56 electrodes 33-145. Data is presented to the output latches from the PA0-PA7 outputs of microprocessor 153 and an address signal is generated by microprocessor 153 on the PB0-PB2 outputs and is transmitted to the A, B and C inputs of decoder 163. The data from microprocessor 153 is clocked in to the respective output latches by means of a logic high level pulse from one of the X1-X7 outputs of decoder 163.

When all of the output latches contained the required data for application to the cardiac mapping system, the microprocessor 153 sets the PCO output thereof to a logic low level for simultaneously enabling the latches via the output enable inputs OE. The data signals are presented via output ports Q0-Q7 to a plurality of wave shaping circuits within a wave shaping board 165.

Each line from respective ones of the output latches is connected to a corresponding RC network within the wave shaping board 165 for attenuating and shaping the received digital pulse into a bipolar pulse of preferably 15 mV amplitude and 5 mS duration. The bipolar pulse waveform closely resembles the electrophysiological signals normally generated by the heart and received via the epicardial bipolar electrodes 33-145.

In accordance with the preferred embodiment, nine maps are generated by the simulator 147 with a 500-mS delay between each map. There is also preferably a 500-mS delay after execution of the last map and before the microprocessor 153 causes flip-flop 161 to open relay K1 for removing power from the simulator.

The vertical map illustrated in FIG. 3 may be generated by the simulator 149 of the present invention in accordance with a pattern of digital signals output from microprocessor 153 and written into respective ones of the output latches such as latch 155 in accordance with a sequence of loading respective ones of the latches as depicted diagrammatically in Table 1.

The latches are designated in Table 1 as latch No. 1 to latch No. 7, and the respective outputs Q0-Q7 of the latches are designated by the labels PA0-PA7 corresponding to the outputs of microprocessor 153. The numbers 1 through 8 shown in Table 1 represent successive instances in time during which respective digital pulses are output from latch No. 1-No. 7.

TABLE 1

| | VERTICAL | | | | | | | |
|---|---|---|---|---|---|---|---|---|
| | PA0 | PA1 | PA2 | PA3 | PA4 | PA5 | PA6 | PA7 |
| LATCH #1 | 1 | 2 | 3 | 4 | 5 | 6 | 7 | 8 |
| LATCH #2 | 1 | 2 | 3 | 4 | 5 | 6 | 7 | 8 |
| LATCH #3 | 1 | 2 | 3 | 4 | 5 | 6 | 7 | 8 |
| LATCH #4 | 1 | 2 | 3 | 4 | 5 | 6 | 7 | 8 |
| LATCH #5 | 1 | 2 | 3 | 4 | 5 | 6 | 7 | 8 |
| LATCH #6 | 1 | 2 | 3 | 4 | 5 | 6 | 7 | 8 |
| LATCH #7 | 1 | 2 | 3 | 4 | 5 | 6 | 7 | 8 |

Thus, in operation, the first step in generating a vertical map comprises generation of eight digital output pulses within the PA0 bit location of each of the output latches and no pulses being generated in the remaining seven bits of each latch. This action causes eight of the 56 output lines from the simulator to present a pulse to the cardiac mapping system (corresponding to electrodes 33-45 shown in FIG. 3).

Next, eight digital output pulses are generated within the PAI bit location of each of the output latches and no pulses being generated in the remaining seven bits of each latch.

This procedure is repeated six more times for successive bits of the output latches (PA2 to PA7) resulting in digital simulation of a vertical map progressing from left to right across the electrode array.

Table 2 below indicates the correspondence between respective outputs of latch No.1–No. 7 in relation to the electrodes 33–145.

TABLE 2

|  | PA0 | PA1 | PA2 | PA3 | PA4 | PA5 | PA6 | PA7 |
| --- | --- | --- | --- | --- | --- | --- | --- | --- |
| LATCH #1 | 33 | 59 | 61 | 87 | 89 | 115 | 117 | 145 |
| LATCH #2 | 35 | 57 | 63 | 85 | 91 | 113 | 119 | 141 |
| LATCH #3 | 37 | 55 | 65 | 83 | 93 | 111 | 121 | 139 |
| LATCH #4 | 39 | 53 | 67 | 81 | 95 | 109 | 123 | 137 |
| LATCH #5 | 41 | 51 | 69 | 79 | 97 | 107 | 125 | 135 |
| LATCH #6 | 43 | 49 | 71 | 77 | 99 | 105 | 127 | 133 |
| LATCH #7 | 45 | 47 | 73 | 75 | 101 | 103 | 129 | 131 |

The simulator of the present invention preferably generates nine successive maps including the vertical map described in Table 1, and horizontal, all channels ON, centered square, logarithmic vertical bars, sequential channel firing, DL logo, checker board and cross maps as described in Tables 3–11 respectively, as follows:

TABLE 3

HORIZONTAL

|  | PA0 | PA1 | PA2 | PA3 | PA4 | PA5 | PA6 | PA7 |
| --- | --- | --- | --- | --- | --- | --- | --- | --- |
| LATCH #1 | 1 | 1 | 1 | 1 | 1 | 1 | 1 | 1 |
| LATCH #2 | 2 | 2 | 2 | 2 | 2 | 2 | 2 | 2 |
| LATCH #3 | 3 | 3 | 3 | 3 | 3 | 3 | 3 | 3 |
| LATCH #4 | 4 | 4 | 4 | 4 | 4 | 4 | 4 | 4 |
| LATCH #5 | 5 | 5 | 5 | 5 | 5 | 5 | 5 | 5 |
| LATCH #6 | 6 | 6 | 6 | 6 | 6 | 6 | 6 | 6 |
| LATCH #7 | 7 | 7 | 7 | 7 | 7 | 7 | 7 | 7 |

TABLE 4

ALL CHANNELS ON

|  | PA0 | PA1 | PA2 | PA3 | PA4 | PA5 | PA6 | PA7 |
| --- | --- | --- | --- | --- | --- | --- | --- | --- |
| LATCH #1 | 1 | 1 | 1 | 1 | 1 | 1 | 1 | 1 |
| LATCH #2 | 1 | 1 | 1 | 1 | 1 | 1 | 1 | 1 |
| LATCH #3 | 1 | 1 | 1 | 1 | 1 | 1 | 1 | 1 |
| LATCH #4 | 1 | 1 | 1 | 1 | 1 | 1 | 1 | 1 |
| LATCH #5 | 1 | 1 | 1 | 1 | 1 | 1 | 1 | 1 |
| LATCH #6 | 1 | 1 | 1 | 1 | 1 | 1 | 1 | 1 |
| LATCH #7 | 1 | 1 | 1 | 1 | 1 | 1 | 1 | 1 |

TABLE 5

CENTRED SQUARE

|  | PA0 | PA1 | PA2 | PA3 | PA4 | PA5 | PA6 | PA7 |
| --- | --- | --- | --- | --- | --- | --- | --- | --- |
| LATCH #1 | 4 | 4 | 4 | 4 | 4 | 4 | 4 | 4 |
| LATCH #2 | 4 | 3 | 3 | 3 | 3 | 3 | 3 | 4 |
| LATCH #3 | 4 | 3 | 2 | 2 | 2 | 2 | 3 | 4 |
| LATCH #4 | 4 | 3 | 2 | 1 | 1 | 2 | 3 | 4 |
| LATCH #5 | 4 | 3 | 2 | 2 | 2 | 2 | 3 | 4 |
| LATCH #6 | 4 | 3 | 3 | 3 | 3 | 3 | 3 | 4 |
| LATCH #7 | 4 | 4 | 4 | 4 | 4 | 4 | 4 | 4 |

TABLE 6

LOGARITHMIC VERTICAL BARS

|  | PA0 | PA1 | PA2 | PA3 | PA4 | PA5 | PA6 | PA7 |
| --- | --- | --- | --- | --- | --- | --- | --- | --- |
| LATCH #1 | 1 | 2 | 3 | 4 | 5 | 6 | 7 | 8 |
| LATCH #2 | 1 | 2 | 3 | 4 | 5 | 6 | 7 | 8 |
| LATCH #3 | 1 | 2 | 3 | 4 | 5 | 6 | 7 | 8 |

TABLE 6-continued

LOGARITHMIC VERTICAL BARS

|  | PA0 | PA1 | PA2 | PA3 | PA4 | PA5 | PA6 | PA7 |
| --- | --- | --- | --- | --- | --- | --- | --- | --- |
| LATCH #4 | 1 | 2 | 3 | 4 | 5 | 6 | 7 | 8 |
| LATCH #5 | 1 | 2 | 3 | 4 | 5 | 6 | 7 | 8 |
| LATCH #6 | 1 | 2 | 3 | 4 | 5 | 6 | 7 | 8 |
| LATCH #7 | 1 | 2 | 3 | 4 | 5 | 6 | 7 | 8 |

For the map pattern illustrated in Table 6, microprocessor 153 executes a delay subroutine for causing the delay time between loading of successive bit locations of the output latches to decrease in an exponential manner.

TABLE 7

SEQUENTIAL CHANNEL FIRING

|  | PA0 | PA1 | PA2 | PA3 | PA4 | PA5 | PA6 | PA7 |
| --- | --- | --- | --- | --- | --- | --- | --- | --- |
| LATCH #1 | 1 | 2 | 3 | 4 | 5 | 6 | 7 | 8 |
| LATCH #2 | 9 | 10 | 11 | 12 | 13 | 14 | 15 | 16 |
| LATCH #3 | 17 | 18 | 19 | 20 | 21 | 22 | 23 | 24 |
| LATCH #4 | 25 | 26 | 27 | 28 | 29 | 30 | 31 | 32 |
| LATCH #5 | 33 | 34 | 35 | 36 | 37 | 38 | 39 | 40 |
| LATCH #6 | 41 | 42 | 43 | 44 | 45 | 46 | 47 | 48 |
| LATCH #7 | 49 | 50 | 51 | 52 | 53 | 54 | 55 | 56 |

TABLE 8

DL LOGO

|  | PA0 | PA1 | PA2 | PA3 | PA4 | PA5 | PA6 | PA7 |
| --- | --- | --- | --- | --- | --- | --- | --- | --- |
| LATCH #1 | 2 | 2 | 2 | 2 | 2 | 2 | 2 | 2 |
| LATCH #2 | 2 | 1 | 1 | 2 | 1 | 2 | 2 | 2 |
| LATCH #3 | 2 | 1 | 2 | 1 | 2 | 1 | 2 | 2 |
| LATCH #4 | 2 | 1 | 2 | 1 | 2 | 1 | 2 | 2 |
| LATCH #5 | 2 | 1 | 2 | 1 | 2 | 1 | 2 | 2 |
| LATCH #6 | 2 | 1 | 1 | 2 | 2 | 1 | 1 | 2 |
| LATCH #7 | 2 | 2 | 2 | 2 | 2 | 2 | 2 | 2 |

TABLE 9

CHECKER BOARD

|  | PA0 | PA1 | PA2 | PA3 | PA4 | PA5 | PA6 | PA7 |
| --- | --- | --- | --- | --- | --- | --- | --- | --- |
| LATCH #1 | 1 | 2 | 1 | 2 | 1 | 2 | 1 | 2 |
| LATCH #2 | 2 | 1 | 2 | 1 | 2 | 1 | 2 | 1 |
| LATCH #3 | 1 | 2 | 1 | 2 | 1 | 2 | 1 | 2 |
| LATCH #4 | 2 | 1 | 2 | 1 | 2 | 1 | 2 | 1 |
| LATCH #5 | 1 | 2 | 1 | 2 | 1 | 2 | 1 | 2 |
| LATCH #6 | 2 | 1 | 2 | 1 | 2 | 1 | 2 | 1 |
| LATCH #7 | 1 | 2 | 1 | 2 | 1 | 2 | 1 | 2 |

TABLE 10

CROSS MAP

|  | PA0 | PA1 | PA2 | PA3 | PA4 | PA5 | PA6 | PA7 |
| --- | --- | --- | --- | --- | --- | --- | --- | --- |
| LATCH #1 | 4 | 3 | 2 | 1 | 1 | 2 | 3 | 4 |
| LATCH #2 | 3 | 3 | 2 | 1 | 1 | 2 | 3 | 3 |
| LATCH #3 | 2 | 2 | 2 | 1 | 1 | 2 | 2 | 2 |
| LATCH #4 | 1 | 1 | 1 | 1 | 1 | 1 | 1 | 1 |
| LATCH #5 | 2 | 2 | 2 | 1 | 1 | 2 | 2 | 2 |
| LATCH #6 | 3 | 3 | 2 | 1 | 1 | 2 | 3 | 3 |
| LATCH #7 | 4 | 3 | 2 | 1 | 1 | 2 | 3 | 4 |

Generation of the sequential pulse trains in Tables 3–10 is interpreted by the cardiac mapping system as being a timing map received from electrodes 33–145. Within the cardiac mapping system, each pulse is assigned an "activation time". This "activation time" is assigned a colour in the output isochronal map. The mapping then creates a map by interpolating colours between the physical spatial location of the successive "activation times". The data from the physical spatial location is obtained by the mapping system from the electrode grid.

As indicated above, there are preferably 9 maps which are generated successively by the simulator of the present invention for testing proper operation of the cardiac mapping system. These 9 maps are preferably executed every time the simulator is activated by depressing the start switch 151. An operator at the data processing computer 17 can choose to generate a particular map by selecting a specific pattern acquired by the mapping system.

The aforementioned nine maps are preferably generated in sequence and spaced approximately 0.5 seconds apart, in the following sequence:
1) All channels simultaneously ON (Table 4)
2) Linear Vertical Bars (Table 1)
4) Centred Square (Table 5)
5) Logarithmic Vertical Bars (Table 6)
6) Sequential Channel Firing (Table 7)
7) DL Logo (Table 8)
8) Checker Board (Table 9)
9) Cross (Table 10)

The microprocessor program for producing the various maps is presented as a source code listing in Appendix I, to which the reader is referred.

Other embodiments or variations of the present invention are contemplated, as follows. The simulator of the present invention may with minor software modifications be used to test equipment in an electrophysiology laboratory. The principal instrument requiring testing in such a laboratory is the amplifier system. The proper functioning of the amplifiers, switching system, digital conversion, etc. of such electrophysiological equipment can be tested with the simulator of the present invention by providing precisely time signals on each of the output channels.

Furthermore, automated systems for interpreting the data gathered by an electrophysiology laboratory system can be provided to receive time coded signals from the simulator in order to execute and test associated algorithms and check the results against known values.

APPENDIX I

LISTING 1.

AVOCET SYSTEMS 6805 CROSS-ASSEMBLER - VERSION 1.08M

SOURCE FILE NAME: SIM.ASM

```
                    ;*****************CARDIAC MAPPING SIMULATOR
                    ;***************** VERSION 1.7
0000

0000

0000            PDRA   EQU   00H
0001            PDRB   EQU   01H
0002            PDRC   EQU   02H
0003            PDRD   EQU   03H
0004            DDRA   EQU   04H
0005            DDRB   EQU   05H
0006            DDRC   EQU   06H
0008            TDR    EQU   08H

000A            MR     EQU   0AH
000E            ACR    EQU   0EH
000F            ARR    EQU   0FH
0009            TCR    EQU   09H
0F38            MOR    EQU   0F38H
000B            PCR    EQU   0BH
0050            TEMP   EQU   0050H
0051            CUR    EQU   0051H
0066            PUTM   EQU   0102  ;PULSE UP TIME (2.5 mS)(DECIMAL)
0052            TMP    EQU   0052H 0000
 0000                   ORG   0
 0000  00               DB    0
 0001
```

;***********************MAINLINE ROUTINE

```
0080                        ORG    0080H      ;EPROM FROM 0080H TO 0F37H
0080 9B                     SEI               ;DISABLE INTERRUPTS
0081 A6FF                   LDA    #0FFH
0083 B704                   STA    DDRA ;PORT A = OUTPUT
0085 B705                   STA    DDRB ;PORT B = OUTPUT
0087 B706                   STA    DDRC ;PORT C = OUTPUT
0089 A600         TEST      LDA    #00
008B B700                   STA    PDRA ;OUTPUT 00 TO PORT A
008D B701                   STA    PDRB ;OUTPUT 00 TO PORT B
008F A601                   LDA    #01
0091 B702                   STA    PDRC ;OUTPUT 01 TO PORT C, DISABLE LATCHES
0093 CD00FB                 JSR    CLEAR
0096 A608                   LDA    #08
0098 B701                   STA    PDRB ;START PULSE FOR MAPPING SYSTEM (PB3)
009A CD0460                 JSR    D100MS    ;DELAY 100 mS
009D A600         OUT1      LDA    #00
```

SOURCE FILE NAME: SIM.ASM

```
009F B701                   STA    PDRB ;BRING START PULSE DOWN
00A1 CD046B                 JSR    WAIT
00A4 CD0112                 JSR    MAP1
00A7 CD00FB                 JSR    CLEAR
00AA CD046B                 JSR    WAIT
00AD CD0126                 JSR    MAP2      ;GENERATE SECOND MAP
00B0 CD00FB                 JSR    CLEAR
00B3 CD046B                 JSR    WAIT
00B6 CD0151                 JSR    MAP3
00B9 CD00FB                 JSR    CLEAR
00BC CD046B                 JSR    WAIT
00BF CD0199                 JSR    MAP4
00C2 CD00FB                 JSR    CLEAR
00C5 CD046B                 JSR    WAIT
00C8 CD0218                 JSR    MAP5
00CB CD00FB                 JSR    CLEAR
00CE CD046B                 JSR    WAIT
00D1 CD0251                 JSR    MAP6
00D4 CD00FB                 JSR    CLEAR
00D7 CD046B                 JSR    WAIT
00DA CD02A0                 JSR    MAP7
00DD CD00FB                 JSR    CLEAR
00E0 CD046B                 JSR    WAIT
00E3 CD0313                 JSR    MAP8
00E6 CD00FB                 JSR    CLEAR
00E9 CD046B                 JSR    WAIT
00EC CD0372                 JSR    MAP9
00EF CD00FB                 JSR    CLEAR
00F2 CD046B                 JSR    WAIT
00F5 A620         END       LDA    #20H
00F7 B701                   STA    PDRB
00F9 BCF5                   JMP    END
00FB
```

;***********************CLEAR, CLEARS ALL LATCHES
```
00FB A600         CLEAR     LDA    #00
00FD B700                   STA    PDRA
00FF AE07         NOCLR     LDX    #07H
```

```
0101 BF01        CLLOOP STX   PDRB  ;OUTPUT LATCH CLOCK PULSE
0103 A602               LDA   #0:.1
0105 CD045A             JSR   DLOOP      ;CLOCK PULSE UP TIME
0108 5A                 DECX         ;NEXT LATCH
0109 2702               BEQ   CLOUT      ;BRANCH IF ALL LATCHES DONE
010B 20F4               BRA   CLLOOP     ;LOOP TO NEXT LATCH
010D A600        CLOUT  LDA   #00
010F B701               STA   PDRB
0111 81                 RTS
0112
```

;********************MAP1, ALL CHANNELS SIMULTANEOUSL

SOURCE FILE NAME: SIM.ASM

```
0112 A6FF        MAP1  LDA   #0FFH
0114 B700              STA   PDRA ;OUTPUT ALL ONES
0116 BDFF              JSR   NOCLR      ;THIS WILL LATCH ALL 1'S
0118 A600              LDA   #00H
011A B702              STA   PDRC ;ENABLE THE LATCH OUTPUTS
011C A666              LDA   #PUTM      ;SET UP FOR A 2.5 mS DELAY
011E CD045A            JSR   DLOOP      ;WITHIN D1MS
0121 A601              LDA   #01H
0123 B702              STA   PDRC ;DISABLES LATCH OUTPUTS
0125 81                RTS
```

;********************MAP2, HORIZONTAL SCAN, FIXED TI

```
0126 A600        MAP2  LDA   #00H
0128 B700              STA   PDRA
012A BDFB              JSR   CLEAR      ;CLEAR ALL LATCHES
012C A601              LDA   #01
012E B750              STA   TEMP ;SAVE LATCH DATA
0130 B700        M2LOOP STA  PDRA ;OUTPUT PULSES TO LATCHES
0132 BDFF              JSR   NOCLR      ;LATCH THE PULSES
0134 A600              LDA   #00H
0136 B702              STA   PDRC ;ENABLE THE LATCHES
0138 A666              LDA   #PUTM      ; PULSE UP 500uS
013A CD045A            JSR   DLOOP      ;PULSE UP TIME
013D A601              LDA   #01H
013F B702              STA   PDRC ;DISABLE THE LATCHES
0141 AE0A              LDX   #010 ;DECIMAL 10
0143 CD0462            JSR   D1LOOP     ;APPROX 10mS BETWEEN PULSES
0146 B650              LDA   TEMP
0148 48                ASLA         ;NEXT PULSE
0149 2505              BCS   M2DONE     ;BRANCH IF MAP2 DONE
014B B750              STA   TEMP
014D CC0130            JMP   M2LOOP     ;LOOP
0150 81        M2DONE  RTS
```

;********************MAP3, VERTICAL SCAN, FIXED TIMI

```
0151 BDFB        MAP3  JSR   CLEAR
0153 A608              LDA   #08
0155 B750              STA   TEMP ;SAVE NUMBER OF 74HC374'S
0157 A600              LDA   #00
```

```
0159 B751            STA   CUR  ;SAVE CURRENT 74HC374 NUMBER
015B A6FF    M3LOOP  LDA   #0FFH
015D B700            STA   PDRA ;DATA OUT LINES = 11111111
015F 9D              NOP
0160 B651            LDA   CUR  ;GET CURRENT LATCH CODE
0162 B701            STA   PDRB ;LATCH CLOCK PULSE UP
0164 9D              NOP
```

SOURCE FILE NAME: SIM.ASM

```
0165 A600            LDA   #00
0167 B701            STA   PDRB ;LATCH CLOCK PULSE DOWN
0169 A600            LDA   #00
016B B702            STA   PDRC ;ENABLE LATCHES
016D A666            LDA   #PUTM
016F CD045A          JSR   DLOOP     ;PULSE UP TIME
0172 A601            LDA   #01
0174 B702            STA   PDRC ;DISIBLE LATCHES
0176 A600            LDA   #00
0178 B700            STA   PDRA ;DATA OUT LINES = 00000000
017A 9D              NOP
017B B651            LDA   CUR  ;GET CURRENT LATCH CODE
017D B701            STA   PDRB ;LATCH CLOCK PULSE UP
017F 9D              NOP
0180 A600            LDA   #00
0182 B701            STA   PDRB ;LATCH CLOCK PULSE DOWN
0184 B651            LDA   CUR
0186 4C              INCA
0187 B751            STA   CUR  ;NEXT LATCH
0189 B650            LDA   TEMP
018B A001            SUB   #01
018D 2709            BEQ   M3OUT     ;BRANCH IF ALL 7 LATCHES DONE
018F B750            STA   TEMP
0191 AE0A            LDX   #010
0193 CD0462          JSR   D1LOOP    ;10mS IN BETWEEN PULSES
0196 20C3            BRA   M3LOOP    ;NEXT LATCH
0198 81      M3OUT   RTS

0199
             ;***********************MAP 4 STAR SCAN (SQUARE), FIXED

0199 BDFB    MAP4    JSR   CLEAR
019B A601            LDA   #01
019D B702            STA   PDRC ;DISABLE LATCHES
             ;----------------------------------------------------
019F A618            LDA   #018H
01A1 B700            STA   PDRA ;FIRST DATA GROUP
01A3 A604            LDA   #04
01A5 CD0450          JSR   LATCH     ;GOES TO LATCH 4
01A8 CD0435          JSR   SQU  ;OUTPUT FIRST SQUARE
             ;----------------------------------------------------
01AB A63C            LDA   #03CH
01AD B700            STA   PDRA ;SECOND DATA GROUP
01AF A603            LDA   #03
01B1 CD0450          JSR   LATCH     ;GOES TO LATCH 3
01B4 A605            LDA   #05
01B6 CD0450          JSR   LATCH     ;GOES TO LATCH 5
01B9 A624            LDA   #024H
01BB B700            STA   PDRA ;SECOND DATA GROUP
01BD A604            LDA   #04
01BF CD0450          JSR   LATCH     ;GOES TO LATCH 4
```

SOURCE FILE NAME: SIM.ASM

```
01C2 CD0435            JSR    SQU    ;OUTPUT SECOND SQUARE
                       ;------------------------------------------------
01C5 A67E              LDA    #07EH
01C7 B700              STA    PDRA   ;THIRD DATA GROUP
01C9 A602              LDA    #02
01CB CD0450            JSR    LATCH       ;GOES TO LATCH 2
01CE A606              LDA    #06
01D0 CD0450            JSR    LATCH       ;GOES TO LATCH 6
01D3 A642              LDA    #042H
01D5 B700              STA    PDRA   ;THIRD DATA GROUP
01D7 A603              LDA    #03
01D9 CD0450            JSR    LATCH       ;GOES TO LATCH 3
01DC A604              LDA    #04
01DE CD0450            JSR    LATCH       ;GOES TO LATCH 4
01E1 A605              LDA    #05
01E3 CD0450            JSR    LATCH       ;GOES   LATCH 5
01E6 CD0435            JSR    SQU    ;OUTPUT T     QUARE
                       ;------------------------------------------------
01E9 A6FF              LDA    #0FFH
01EB B700              STA    PDRA   ;FOURTH D      UP
01ED A601              LDA    #01
01EF CD0450            JSR    LATCH       ;GOES     TCH 1
01F2 A607              LDA    #07
01F4 CD0450            JSR    LATCH       ;GOES     TCH 7
01F7 A681              LDA    #081H
01F9 B700              STA    PDRA   ;FOURTH DA      P
01FB A602              LDA    #02
01FD CD0450            JSR    LATCH       ;GOES     H 2
0200 A603              LDA    #03
0202 CD0450            JSR    LATCH       ;GOES      3
0205 A604              LDA    #04
0207 CD0450            JSR    LATCH       ;GOE       4
020A A605              LDA    #05
020C CD0450            JSR    LATCH       ;GOE
020F A606              LDA    #06
0211 CD0450            JSR    LATCH       ;GOE
0214 CD0435            JSR    SQU    ;OUTPUT F
                       ;------------------------------------------------
0217 81                RTS

;*********************       SCAN EXPONENTIA
                       G

0218 A600       MAP5   LDA    #00
021A B701              STA    PDRB
021C A680              LDA    #080H       ;THE IN         ETWEEN TIME
021E B750              STA    TEMP   ;SAVE IT
0220 A601              LDA    #01    ;THE INITIAL      DATA
0222 B751              STA    CUR    ;SAVE IT
0224 B700       M5LOOP STA    PDRA   ;LATCH        O PORT A
```

SOURCE FILE NAME: SIM.ASM

```
0226 BDFF              JSR    NOCLR       ;SAVE IT TO THE LATCHES
0228 A600              LDA    #00
```

```
022A B701              STA    PDRB
022C B702              STA    PDRC  ;ENABLE LATCH OUTPUTS
022E A666              LDA    #PUTM      ;GET PULSE UP TIME
0230 CD045A            JSR    DLOOP      ;DELAY
0233 A601              LDA    #01
0235 B702              STA    PDRC  ;DISABLE LATCH OUTPUTS
0237 BE50              LDX    TEMP  ;GET EXP DELAY TIME
0239 CD0458   EXLOOP   JSR    D1MS  ;DELAY FOR 1MS
023C 5A                DEX          ;DECREMENT X COUNTER
023D 26FA              BNE    EXLOOP     ;BRANCH IF DELAY NOT DONE
023F B650              LDA    TEMP
0241 44                LSRA         ;NEXT DELAY TIME
0242 2502              BCS    GOUT  ;BRANCH IF ALL 8 DONE
0244 2001              BRA    GO
0246 81       GOUT RTS
0247 B750     GO       STA    TEMP  ;SAVE NEW DELAY TIME
0249 B651              LDA    CUR   ;GET CURRENT LATCH DATA
024B 48                ASLA         ;NEXT LATCH DATA
024C B751              STA    CUR   ;SAVE IT
024E CC0224            JMP    M5LOOP     ;NEXT PULSE

;********************MAP 6 (ALL CHANNELS 5mS APPART)

0251 A607     MAP6     LDA    #07
0253 B750              STA    TEMP  ;7 LATCHES TO DO
0255 A601              LDA    #01
0257 B751              STA    CUR   ;THE CURRENT LATCH
0259 A601              LDA    #01
025B B752              STA    TMP   ;CURRENT DATA OUTPUT
025D B652     LP6      LDA    TMP
025F B700              STA    PDRA  ;OUTPUT DATA
0261 9D                NOP
0262 B651              LDA    CUR
0264 B701              STA    PDRB  ;CURRENT LATCH CODE
0266 9D                NOP
0267 A600              LDA    #00
0269 B701              STA    PDRB  ;LATCH PULSE DOWN
026B A600              LDA    #00
026D B702              STA    PDRC  ;ENABLE LATCHES
026F A666              LDA    #PUTM
0271 CD045A            JSR    DLOOP ;PULSE UP TIME
0274 A601              LDA    #01
0276 B702              STA    PDRC  ;DISABLE LATCHES
0278 BDFB              JSR    CLEAR
027A AE0A              LDX    #010
027C CD0462            JSR    D1LOOP;10 mS DELAY BETWEEN PULSES
027F B652              LDA    TMP
0281 48                ASLA
```

SOURCE FILE NAME: SIM.ASM

```
0282 2505              BCS    SMGO  ;BRANCH IF ALL 8 LINES DONE
0284 B752              STA    TMP   ;SAVE CURRENT DATA
0286 CC025D            JMP    LP6   ;LOOP TO NEXT DATA
0289 BDFB     SMGO JSR CLEAR
028B B650              LDA    TEMP
028D A001              SUB    #01
028F 270E              BEQ    M6DN
0291 B750              STA    TEMP
```

```
0293 B651           LDA  CUR
0295 4C             INCA      ;NEXT LATCH
0296 B751           STA  CUR
0298 A601           LDA  #01
029A B752           STA  TMP
029C CC025D         JMP  LP6  ;LOOP
029F 81       M6DN  RTS
02A0
02A0

;***********************MAP 7 "DL"

02A0 BDFB     MAP7  JSR  CLEAR
02A2 A601           LDA  #01
02A4 B702           STA  PDRC ;DISABLE LATCHES
02A6 A600           LDA  #00H
02A8 B700           STA  PDRA
02AA A601           LDA  #01
02AC CD0450         JSR  LATCH;00H TO LATCH #1
02AF A607           LDA  #07
02B1 CD0450         JSR  LATCH;00H TO LATCH #7
02B4 A626           LDA  #026H
02B6 B700           STA  PDRA
02B8 A602           LDA  #02
02BA CD0450         JSR  LATCH;26H TO LATCH #2
02BD A62A           LDA  #02AH
02BF B700           STA  PDRA
02C1 A603           LDA  #03
02C3 CD0450         JSR  LATCH;2AH TO LATCH #3
02C6 A604           LDA  #04
02C8 CD0450         JSR  LATCH;2AH TO LATCH #4
02CB A605           LDA  #05
02CD CD0450         JSR  LATCH;2AH TO LATCH #5
02D0 A666           LDA  #066H
02D2 B700           STA  PDRA
02D4 A606           LDA  #06
02D6 CD0450         JSR  LATCH;66H TO LATCH #6
02D9 CD0435         JSR  SQU  ;OUTPUT FIRST PULSES
02DC A6FF           LDA  #0FFH
02DE B700           STA  PDRA
02E0 A601           LDA  #01
02E2 CD0450         JSR  LATCH;FFH TO LATCH #1
02E5 A607           LDA  #07
02E7 CD0450         JSR  LATCH;FFH TO LATCH #7
```

SOURCE FILE NAME. SIM.ASM

```
02EA A6D9           LDA  #0D9H
02EC B700           STA  PDRA
02EE A602           LDA  #02
02F0 CD0450         JSR  LATCH;D9H TO LATCH #2
02F3 A6D5           LDA  #0D5H
02F5 B700           STA  PDRA
02F7 A603           LDA  #03
02F9 CD0450         JSR  LATCH;D5H TO LATCH #3
02FC A604           LDA  #04
02FE CD0450         JSR  LATCH;D5H TO LATCH #4
0301 A605           LDA  #05
0303 CD0450         JSR  LATCH;D5H TO LATCH #5
```

```
0306 A699             LDA   #099H
0308 B700             STA   PDRA
030A A606             LDA   #06
030C CD0450           JSR   LATCH;99H TO LATCH #6
030F CD0435           JSR   SQU  ;OUTPUT SECOND PULSES
0312 81               RTS
0313
```

;************************MAP 8 (CHECKER BOARD)

```
0313 BDFB       MAP8  JSR   CLEAR
0315 A655             LDA   #055H
0317 B700             STA   PDRA
0319 A601             LDA   #01
031B CD0450           JSR   LATCH;55H TO LATCH #1
031E A603             LDA   #03
0320 CD0450           JSR   LATCH;55H TO LATCH #3
0323 A605             LDA   #05
0325 CD0450           JSR   LATCH;55H TO LATCH #5
0328 A607             LDA   #07
032A CD0450           JSR   LATCH;55H TO LATCH #7
032D A6AA             LDA   #0AAH
032F B700             STA   PDRA
0331 A602             LDA   #02
0333 CD0450           JSR   LATCH;AAH TO LATCH #2
0336 A604             LDA   #04
0338 CD0450           JSR   LATCH;AAH TO LATCH #4
033B A606             LDA   #06
033D CD0450           JSR   LATCH;AAH TO LATCH #6
0340 CD0435           JSR   SQU  ;OUTPUT FIRST PULSES
0343 A6AA             LDA   #0AAH
0345 B700             STA   PDRA
0347 A601             LDA   #01
0349 CD0450           JSR   LATCH;AAH TO LATCH #1
034C A603             LDA   #03
034E CD0450           JSR   LATCH;AAH TO LATCH #3
0351 A605             LDA   #05
0353 CD0450           JSR   LATCH;AAH TO LATCH #5
0356 A607             LDA   #07
```

SOURCE FILE NAME: SIM.ASM

```
0358 CD0450           JSR   LATCH;AAH TO LATCH #7
035B A655             LDA   #055H
035D B700             STA   PDRA
035F A602             LDA   #02
0361 CD0450           JSR   LATCH;55H TO LATCH #2
0364 A604             LDA   #04
0366 CD0450           JSR   LATCH;55H TO LATCH #4
0369 A606             LDA   #06
036B CD0450           JSR   LATCH;55H TO LATCH #6
036E CD0435           JSR   SQU  ;OUTPUT SECOND PULSES
0371 81               RTS
```

;************************MAP 9 (CROSS PATTERN)

```
0372 BDFB       MAP9  JSR   CLEAR
0374 A618             LDA   #018H
```

```
0376 B700              STA   PDRA
0378 A601              LDA   #01
037A CD0450            JSR   LATCH;18H TO LATCH #1
037D A602              LDA   #02
037F CD0450            JSR   LATCH;18H TO LATCH #2
0382 A603              LDA   #03
0384 CD0450            JSR   LATCH;18H TO LATCH #3
0387 A605              LDA   #05
0389 CD0450            JSR   LATCH;18H TO LATCH #5
038C A606              LDA   #06
038E CD0450            JSR   LATCH;18H TO LATCH #6
0391 A607              LDA   #07
0393 CD0450            JSR   LATCH;18H TO LATCH #7
0396 A6FF              LDA   #0FFH
0398 B700              STA   PDRA
039A A604              LDA   #04
039C CD0450            JSR   LATCH;FFH TO LATCH #4
039F CD0435            JSR   SQU  ;OUTPUT FIRST PULSES
03A2 A624              LDA   #024H
03A4 B700              STA   PDRA
03A6 A601              LDA   #01
03A8 CD0450            JSR   LATCH;24H TO LATCH #1
03AB A602              LDA   #02
03AD CD0450            JSR   LATCH;24H TO LATCH #2
03B0 A606              LDA   #06
03B2 CD0450            JSR   LATCH;24H TO LATCH #6
03B5 A607              LDA   #07
03B7 CD0450            JSR   LATCH;24H TO LATCH #7
03BA A6E7              LDA   #0E7H
03BC B700              STA   PDRA
03BE A603              LDA   #03
03C0 CD0450            JSR   LATCH;E7H TO LATCH #3
03C3 A605              LDA   #05
03C5 CD0450            JSR   LATCH;E7H TO LATCH #5

SOURCE FILE NAME: SIM.ASM

03C8 A600              LDA   #00H
03CA B700              STA   PDRA
03CC A604              LDA   #04
03CE CD0450            JSR   LATCH;00H TO LATCH #4
03D1 CD0435            JSR   SQU  ;OUTPUT SECOND PULSES
03D4 A642              LDA   #042H
03D6 B700              STA   PDRA
03D8 A601              LDA   #01
03DA CD0450            JSR   LATCH;42H TO LATCH #1
03DD A607              LDA   #07
03DF CD0450            JSR   LATCH;42H TO LATCH #7
03E2 A6C3              LDA   #0C3H
03E4 B700              STA   PDRA
03E6 A602              LDA   #02
03E8 CD0450            JSR   LATCH;C3H TO LATCH #2
03EB A606              LDA   #06
03ED CD0450            JSR   LATCH;C3H TO LATCH #6
03F0 A600              LDA   #00H
03F2 B700              STA   PDRA
03F4 A603              LDA   #03
03F6 CD0450            JSR   LATCH;00H TO LATCH #3
03F9 A604              LDA   #04
```

```
03FB CD0450            JSR    LATCH;00H TO LATCH #4
03FE A605              LDA    #05
0400 CD0450            JSR    LATCH;00H TO LATCH #5
0403 CD0435            JSR    SQU  ;OUTPUT THIRD PULSES
0406 A681              LDA    #81H
0408 B700              STA    PDRA
040A A601              LDA    #01
040C CD0450            JSR    LATCH;81H TO LATCH #1
040F A607              LDA    #07
0411 CD0450            JSR    LATCH;81H TO LATCH #7
0414 A600              LDA    #00H
0416 B700              STA    PDRA
0418 A602              LDA    #02
041A CD0450            JSR    LATCH;00H TO LATCH #2
041D A603              LDA    #03
041F CD0450            JSR    LATCH;00H TO LATCH #3
0422 A604              LDA    #04
0424 CD0450            JSR    LATCH;00H TO LATCH #4
0427 A605              LDA    #05
0429 CD0450            JSR    LATCH;00H TO LATCH #5
042C A606              LDA    #06
042E CD0450            JSR    LATCH;00H TO LATCH #6
0431 CD0435            JSR    SQU  ;OUTPUT FOURTH PULSES
0434 81                RTS

;************************OUTPUT SQUARE SUBROUTINE

0435 A600       SQU    LDA    #00

SOURCE FILE NAME: SIM.ASM

0437 B700              STA    PDRA ;DATA GROUP OFF
0439 B702              STA    PDRC ;SQUARE ENABLED
043B A666              LDA    #PUTM
043D CD045A            JSR    DLOOP      ;SQUARE ON TIME
0440 A601              LDA    #01
0442 B702              STA    PDRC ;SQUARE DISABLED
0444 BDFB              JSR    CLEAR      ;CLEAR THE LATCHES
0446 A600              LDA    #00
0448 B701              STA    PDRB
044A AE0A              LDX    #010
044C CD0462            JSR    D1LOOP     ;10 mS DELAY BETWEEN PULSES
044F 81                RTS

0450
                       ;************************LATCH SUBROUTINE

0450 B701       LATCH  STA    PDRB ;LATCH PULSE UP
0452 9D                NOP
0453 A600              LDA    #00
0455 B701              STA    PDRB ;LATCH PULSE DOWN
0457 81                RTS
0458
0458
                       ;**********************1MS DELAY    OUTINE (DESTROYS T

0458 A629       D1MS   LDA    #41  ;DECIMAL 41 IS THE      OUNT
045A 4A         DLOOP  DECA
```

```
045B 2702              BEQ    DDONE       ;BRANCH IF DONE
045D 20FB              BRA    DLOOP       ;LOOP
045F 81        DDONE   RTS                ;RETURN FROM SUBROUTINE

;********************100MS DELAY SUBROUTINE (DESTROYS
        ' & `X')

0460 AE64      D100MS  LDX    #100        ;DECIMAL
0462 5A        D1LOOP  DECX
0463 2705              BEQ    D1OUT       ;BRANCH IF
0465 CD0458            JSR    D1MS        ;DELAY 1MS
0468 20F8              BRA    D1LOOP
046A 81        D1OUT   RTS

;********************WAIT SUBROUTINE (.5 SECOND DELAY)

046B A605      WAIT    LDA    #05H
046D B750      WLOOP   STA    TEMP
046F CD0460            JSR    D100MS      ;DELAY 100MS
0472 B650              LDA    TEMP
0474 4A                DECA
0475 26F6              BNE    WLOOP       ;BRANCH IF NOT DONE 1S 0477 81                RTS
0478

;********************INTERRUPT VECTORS

0FF8                   ORG    0FF8H
0FF8 0080              DW     0080H
0FFA 0080              DW     0080H
0FFC 0080              DW     0080H
0FFE 0080              DW     0080H

0080                   END    0080H
```

SOURCE FILE NAME: SIM.ASM
---- SYMBOL TABLE ----

| | | | | | |
|---|---|---|---|---|---|
| ACR | 000E | LATCH | 0450 | NOCLR | 00FF |
| ARR | 000F | LP6 | 025D | OUT1 | 009D |
| CLEAR | 00FB | M2DONE | 0150 | PCR | 000B |
| CLLOOP | 0101 | M2LOOP | 0130 | PDRA | 0000 |
| CLOUT | 010D | M3LOOP | 015B | PDRB | 0001 |
| CUR | 0051 | M3OUT | 0198 | PDRC | 0002 |
| D100MS | 0460 | M5LOOP | 0224 | PDRD | 0003 |
| D1LOOP | 0462 | M6DN | 029F | PUTM | 0066 |
| D1MS | 0458 | MAP1 | 0112 | SMGO | 0289 |
| D1OUT | 046A | MAP2 | 0126 | SQU | 0435 |
| DDONE | 045F | MAP3 | 0151 | TCR | 0009 |
| DDRA | 0004 | MAP4 | 0199 | TDR | 0008 |
| DDRB | 0005 | MAP5 | 0218 | TEMP | 0050 |
| DDRC | 0006 | MAP6 | 0251 | TEST | 0089 |
| DLOOP | 045A | MAP7 | 02A0 | TMP | 0052 |
| END | 00F5 | MAP8 | 0313 | WAIT | 046B |
| EXLOOP | 0239 | MAP9 | 0372 | WLOOP | 046D |
| GO | 0247 | MOR | 0F38 | | |
| GOUT | 0246 | MR | 000A | | |

All such variations and modifications are believed to be within the sphere and scope of the present invention as defined by the claims appended hereto.

We claim:

1. A biomedical mapping simulator for generating a pattern of simulated electrophysiological impulses corresponding to a two-dimensional timing map for application to an electrophysiological impulse display device, comprising:
   (a) programmable means for generating a succession of digital signals,
   (b) circuit means for receiving said succession of digital signals and in response generating a succession of output signals on predetermined outputs thereof, said outputs being arranged to form a two-dimensional array, and
   (c) means for shaping said output signals to resemble said electrophysiological impulses and applying the shaped output signals to said display device, said shaped output signals representing isochronal lines on said timing map.

2. An apparatus as defined in claim 1, wherein said programmable means further comprises a microprocessor programmed for generating said digital signals.

3. An apparatus as defined in claim 2, wherein said circuit means further comprises:
   (a) a plurality of latches for receiving and latching said succession of digital signals, and
   (b) means for enabling respective ones of said plurality of latches according to a predetermined sequence for generating said succession of output signals.

4. An apparatus as defined in claim 3, wherein respective ones of said latches correspond to respective rows in said array and successive outputs of each said latches correspond to respective column elements in corresponding ones of said rows.

5. An apparatus as defined in claim 3, wherein said means for enabling further comprises a decoder for receiving predetermined additional digital signals from said programmable means and in response generating predetermined select signals for enabling said respective ones of said plurality of latches.

6. An apparatus as defined in claim 1, wherein said means for shaping further comprises a plurality of RC networks for filtering said output signals and in response generating respective bipolar pulses resembling said electrophysiological impulses.

7. An apparatus as defined in claim 1, further comprising means for applying operating power to said programmable means and said circuit means for a predetermined length of time sufficient to generate said output signals, and thereafter ceasing application of said operating power to said programmable means and said circuit means.

8. An apparatus as defined in claim 1, wherein said circuit means further comprises seven 8-bit latches for generating said output signals associated with seven respective rows of said array, each of said rows comprising eight elements corresponding to respective outputs of said latches.

9. A method for generating a pattern of simulated electrophysiological impulses corresponding to a two-dimensional timing map, comprising the steps of:
   (a) generating one or more sequences of digital signals,
   (b) loading said one or more sequences of digital signals into predetermined bit locations of a plurality of latches, said bit locations of respective ones of said latches being arranged to form a two-dimensional array, and
   (c) shaping said digital signals to resemble electrophysiological impulses, said shaped digital signals representing isochronal lines on said timing map.

10. A method as defined in claim 9, further comprising the step of loading a sequence of logic high digital signals into each bit location of each of said latches, whereby a pattern of logic high impulses is generated within said array.

11. A method as defined in claim 9, further comprising the step of arranging said latches into seven rows of eight bit locations each.

12. A method for generating a series of simulated electrophysiological impulses in two dimensions, comprising the steps of:
   (a) generating one or more sequences of digital signals,
   (b) loading said one or more sequences of digital signals into predetermined bit locations of a plurality of latches, said bit locations of respective ones of said latches being arranged to form a two-dimensional array,
   (c) shaping said digital signals to resemble electrophysiological impulses, whereby said sequences of digital signals form a two-dimensional pattern of said simulated electrophysiological impulses,
   (d) loading a sequence of logic high digital signals into a least significant bit location of each of said latches, and loading a sequence of logic low digital signals into remaining ones of said bit locations, and
   (e) successively loading said sequence of logic high digital signals into successively more significant bit location of each of said latches, and loading said sequence of logic low digital signals into the remaining ones of bit locations, whereby a moving vertical pattern of said impulses is generated within said array.

13. A method for generating a series of simulated electrophysiological impulses in two dimensions, comprising the steps of:
   (a) generating one or more sequences of digital signals,
   (b) loading said one or more sequences of digital signals into predetermined bit locations of a plurality of latches, said bit locations of respective ones of said latches being arranged to form a two-dimensional array,
   (c) shaping said digital signals to resemble electrophysiological impulses, whereby said sequences of digital signals form a two-dimensional patter of said simulated electrophysiological impulses,
   (d) loading a sequence of logic high digital signals into a first one of said latches, and loading a sequence of logic low level signals into remaining ones of said latches, and
   (e) successively loading said sequence of logic high digital signals into successive ones of said latches, and loading said sequence of logic low digital signals into the remaining ones of said latches, whereby a moving horizontal pattern of said impulses is generated within said array.

14. A method for generating a series of simulated electrophysiological impulses in two dimensions, comprising the steps of:
   (a) generating one or more sequences of digital signals, (b) loading said one or more sequences of digital signals into predetermined bit locations of a plurality of latches, said bit locations of respective ones of said latches being arranged to form a two-dimensional array, (c) shaping said digital signals to resemble electrophysiological impulses, whereby said sequences of digital signals form a two-dimensional pattern of said simulated electrophysiological impulses, (d) arranging said latches into seven rows of eight bit locations each, (e) loading a first one of said latches corresponding to the fourth one of said rows with a digital signal having a value of 04 hex, (f) loading second and third ones of said latches corresponding to the third and fifth ones of said rows with a digital signal having a value of 03 hex, (g) loading said first one of said latches with a digital signal having a value of 04 hex, (h) loading fourth and fifth ones of said latches corresponding to the second and sixth ones of said rows with a digital signal having a value of 7E hex, (i) loading said first, second and third latches with a digital signal having a value of 42 hex, (j) loading sixth and seventh ones of said latches corresponding to the first and seventh ones of said rows with a digital signal having a value of FF hex, and (k) loading said first, second, third, fourth and fifth latches with a digital signal having a value of 81 hex, whereby a moving square pattern of said impulses is generated within said array.

15. A method for generating a series of simulated electrophysiological impulses in two dimensions, comprising the steps of:

(a) generating one or more sequences of digital signals, (b) loading said one or more sequences of digital signals into predetermined bit locations of a plurality of latches, said bit locations of respective ones of said latches being arranged to form a two-dimensional array, (c) shaping said digital signals to resemble electrophysiological impulses, whereby said sequences of digital signals form a two-dimensional pattern of said simulated electrophysiological impulses, (d) arranging said latches into seven rows of eight bit locations each, and (e) successively loading progressively more significant bit locations of respective ones of said latches with a logic high digital signal, and loading a sequence of logic low digital signals into remaining ones of said bit locations, whereby a moving signal impulse pattern is generated across successive elements of said array.

16. A method for generating a series of simulated electrophysiological impulses in two dimensions, comprising the steps of:

(a) generating one or more sequences of digital signals, (b) loading said one or more sequences of digital signals into predetermined bit locations of a plurality of latches, said bit locations of respective ones of said latches being arranged to form a two-dimensional array, (c) shaping said digital signals to resemble electrophysiological impulses, whereby said sequences of digital signals form a two-dimensional pattern of said simulated electrophysiological impulses, (d) arranging said latches into seven rows of eight bit locations each, (e) loading first and second ones of said latches corresponding to the first and seventh ones of said rows with a digital signal having a value of 00 hex, (f) loading a third one of said latches corresponding to the second one of said rows with a digital signal having a value of 26 hex, (g) loading fourth, fifth and sixth ones of said latches corresponding to the third, fourth and fifth ones of said rows respectively with a digital signal having a value of 2A hex, (h) loading a seventh one of said latches corresponding to the sixth one of said rows with a digital signal having a value of 66 hex, (i) loading said first and second ones of said latches with a digital signal having a value of FF hex, (j) loading said third one of said latches with a digital signal having a value of D9 hex, (k) loading said fourth, fifth and sixth ones of said latches with a digital signal having a value of D5 hex, and (l) loading said seventh one of said latches with a digital signal having a value of 99 hex, whereby a two-dimensional pattern of said impulses resembling the letters DL is generated within said array.

17. A method for generating a series of simulated electrophysiological impulses in two dimensions, comprising the steps of:

(a) generating one or more sequences of digital signals, (b) loading said one or more sequences of digital signals into predetermined bit locations of a plurality of latches, said bit locations of respective ones of said latches being arranged to form a two-dimensional array, (c) shaping said digital signals to resemble electrophysiological impulses, whereby said sequences of digital signals form a two-dimensional pattern of said simulated electrophysiological impulses, (d) arranging said latches into seven rows of eight bit locations each, (e) loading first, second, third and fourth ones of said latches corresponding to the first, third, fifth and seventh ones of said rows respectively with a digital signal having a value of 55 hex, (f) loading fifth, sixth and seventh ones of said latches corresponding to the second, fourth and sixth ones of said rows respectively with a digital signal having a value of AA hex, (g) loading said first, second, third and fourth ones of said latches with a digital signal having a value of AA hex, and (h) loading said fifth, sixth and seventh latches with a digital signal having a value of 55 hex, whereby a moving checker board pattern of said impulses is generated within said array.

18. A method for generating a series of simulated electrophysiological impulses in two dimensions, comprising the steps of:

(a) generating one or more sequences of digital signals, (b) loading said one or more sequences of digital signals into predetermined bit locations of a plurality of latches, said bit locations of respective ones of said latches being arranged to form a two-dimensional array, (c) shaping said digital signals to resemble electrophysiological impulses, whereby said sequences of digital signals form a two-dimensional pattern of said simulated electrophysiological impulses, (d) arranging said latches into seven rows of eight bit locations each, (e) loading first, second, third, fourth, fifth and sixth ones of said latches corresponding to the first, second, third, fifth, sixth and seventh ones of said rows respectively with a digital signal having a value of 18 hex, (f) loading a seventh one of said latches corresponding to the fourth one of said rows with a digital signal having a value of FF hex, (g) loading said first, second, fifth and sixth latches with a digital signal having a value of 24 hex, (h) loading said third and fourth latches with a digital signal having a value of E7 hex, (i) loading said seventh latch with a digital signal having a value of 00 hex, (j) loading said first and sixth ones of said latches with a digital signal having a value of 42 hex, (k) loading said second and fifth ones of said latches with a digital signal having a value of C3 hex, (l) loading said third, fourth and seventh ones of said latches with a digital signal having a value of 00 hex, (m) loading said first and sixth ones of said latches with a digital signal having a value of 81 hex, and (n) loading said second, third, fourth, fifth and seventh ones of said latches with a digital signal having a value of 00 hex, whereby a moving cross pattern of said impulses is generated within said array.

* * * * *

UNITED STATES PATENT AND TRADEMARK OFFICE
CERTIFICATE OF CORRECTION

PATENT NO.   : 5,041,973
DATED        : August 20, 1991
INVENTOR(S)  : Lebron et al.

It is certified that error appears in the above-identified patent and that said Letters Patent is hereby corrected as shown below:

At column 5, line 32, delete "Closing" and substitute --closing-- therefore.

At column 5, line 59, delete "Connected Via" and substitute --connected via-- therefore.

At column 10, after line 21, add the following new paragraph:

--All such variations and modifications are believed to be within the sphere and scope of the present invention as defined by the claims appended hereto.--

Delete columns 11 and 12 in their entirety and substitute the following therefore:

```
--                       ;******************MAINLINE ROUTINE

0080                                ORG  0080H ;EPROM FROM 0080H TO 0F37H
0080   9B                  SEI             ;DISABLE INTERRUPTS
0081   A6FF                LDA   #0FFH
0083   B704                STA   DDRA      ;PORT A = OUTPUT
0085   B705                STA   DDRB      ;PORT B = OUTPUT
0087   B706                STA   DDRC      ;PORT C = OUTPUT
0089   A600        TEST    LDA   #00
008B   B700                STA   PDRA      ;OUTPUT 00 TO PORT A
008D   B701                STA   PDRB      ;OUTPUT 00 TO PORT B
008F   A601                LDA   #01
0091   B702                STA   PDRC      ;OUTPUT 01 TO PORT C, DISABLE LATCHES
0093   CD00FB              JSR   CLEAR
0096   A608                LDA   #08
0098   B701                STA   PDRB      ;START PULSE FOR MAPPING SYSTEM (PB3)
009A   CD0460              JSR   D100MS    ;DELAY 100 mS
```

UNITED STATES PATENT AND TRADEMARK OFFICE
CERTIFICATE OF CORRECTION

PATENT NO. : 5,041,973
DATED : August 20, 1991
INVENTOR(S) : Lebron et al.

It is certified that error appears in the above-identified patent and that said Letters Patent is hereby corrected as shown below:

```
009D    A600        OUT1    LDA     #00
009F    B701                STA     PDRB    ;BRING START PULSE DOWN
00A1    CD046B              JSR     WAIT
00A4    CD0112              JSR     MAP1
00A7    CD00FB              JSR     CLEAR
00AA    CD046B              JSR     WAIT
00AD    CD0126              JSR     MAP2    ;GENERATE SECOND MAP
00B0    CD00FB              JSR     CLEAR
00B3    CD046B              JSR     WAIT
00B6    CD0151              JSR     MAP3
00B9    CD00FB              JSR     CLEAR
00BC    CD046B              JSR     WAIT
00BF    CD0199              JSR     MAP4
00C2    CD00FB              JSR     CLEAR
00C5    CD046B              JSR     WAIT
00C8    CD0218              JSR     MAP5
00CB    CD00FB              JSR     CLEAR
00CE    CD046B              JSR     WAIT
00D1    CD0251              JSR     MAP6
00D4    CD00FB              JSR     CLEAR
00D7    CD046B              JSR     WAIT
00DA    CD02A0              JSR     MAP7
00DD    CD00FB              JSR     CLEAR
00E0    CD046B              JSR     WAIT
00E3    CD0313              JSR     MAP8
00E6    CD00FB              JSR     CLEAR
00E9    CD046B              JSR     WAIT
00EC    CD0372              JSR     MAP9
00EF    CD00FB              JSR     CLEAR
00F2    CD046B              JSR     WAIT
00F5    A620        END     LDA     #20H
00F7    B701                STA     PDRB
00F9    BCF5                JMP     END
00FB
```

UNITED STATES PATENT AND TRADEMARK OFFICE
CERTIFICATE OF CORRECTION

PATENT NO.  : 5,041,973

DATED       : August 20, 1991

INVENTOR(S) : Lebron et al.

It is certified that error appears in the above-identified patent and that said Letters Patent is hereby corrected as shown below:

```
                      ;*******************CLEAR, CLEARS ALL LATCHES
   00FB   A600   CLEAR       LDA   #00
   00FD   B700               STA   PDRA
   00FF   AE07   NOCLR       LDX   #07H--
```

Delete columns 13 and 14 in their entirety and substitute the following therefore:

```
--0101   BF01    CLLOOP       STX   PDRB  ;OUTPUT LATCH LOCK PULSE
  0103   A602                 LDA   #02H
  0105   CD045A               JSR   DLOOP     ;CLOCK PULSE UP TIME
  0108   5A                   DECX            ;NEXT LATCH
  0109   2702                 BEQ   CLOUT     ;BRANCH IF ALL LATCHES DONE
  010B   20F4                 BRA   CLLOOP    ;LOOP TO NEXT LATCH
  010D   A600    CLOUT        LDA   #00
  010F   B701                 STA   PDRB
  0111   81                   RTS
  0112
                      ;******************MAP1, ALL CHANNELS SIMULTANEOUSL

0112   A6FF    MPA1 LDA     #0FFH
  0114   B700         STA     PDRA      ;OUTPUT ALL ONES
  0116   BDFF         JSR     NOCLR     ;THIS WILL LATCH ALL 1'S
  0118   A600         LDA     #00H
  011A   B702         STA     PDRC      ;ENABLE THE LATCH OUTPUTS
  011C   A666         LDA     #PUTM     ;SET UP FOR A 2.5 mS DELAY
  011E   CD045A       JSR     DLOOP     ;WITHIN D1MS
  0121   A601         LDA     #01H
  0123   B702         STA     PDRC      ;DISABLES LATCH OUTPUTS
  0125   81           RTS
                      ;******************MAP2, HORIZONTAL SCAN, FIXED TIM

0126   A600    MAP2 LDA     #00H
  0128   B700         STA     PDRA
  012A   BDFB         JSR     CLEAR     ;CLEAR ALL LATCHES
  012C   A601         LDA     #01
```

UNITED STATES PATENT AND TRADEMARK OFFICE
CERTIFICATE OF CORRECTION

PATENT NO. : 5,041,973
DATED : August 20, 1991
INVENTOR(S) : Lebron et al.

It is certified that error appears in the above-identified patent and that said Letters Patent is hereby corrected as shown below:

```
     012E    B750              STA    TEMP     ;SAVE LATCH DATA
     0130    B700    MSLOOP    STA    PDRA     ;OUTPUT PULSES TO LATCHES
     0132    BDFF              JSR    NOCLR    ;LATCH THE PULSES
     0134    A600              LDA    #00H
     0136    B702              STA    PDRC     ;ENABLE THE LATCHES
     0138    A666              LDA    #PUTM    ;PULSE UP 500uS
     013A    CD045A            JSR    DLOOP    ;PULSE UP TIME
     013D    A601              LDA    #01H
     013F    B702              STA    PDRC     ;DISABLE THE LATCHES
     0141    AEOA              LDX    #010     ;DECIMAL 10
     0143    CD0462            JSR    D1LOOP   ;APPROX 10mS BETWEEN PULSES
     0146    B650              LDA    TEMP
     0148    48                ASLA            ;NEXT PULSE
     0149    2505              BCS    M2DONE   ;BRANCH IF MAP2 DONE
     014B    B750              STA    TEMP
     014D    CC0130            JMP    M2LOOP   ;LOOP
     0150    81      M2DONE    RTS

;********************MAP3, VERTICAL SCAN, FIXED TIMIN

0151    BDFB    MAP3      JSR    CLEAR
     0153    A608              LDA    #08
     0155    B750              STA    TEMP     ;SAVE NUMBER OF 74HC374'S
     0157    A600              LDA    #00--
```

Delete columns 15 and 16 in their entirety and substitute the following therefore:

```
   --0159    B751              STA    CUR      ;SAVE CURRENT 74HC374 NUMBER
     015B    A6FF    M3LOOP    LDA    #0FFH
     015D    B700              STA    PDRA     ;DATA OUT LINES = 11111111
     015F    9D                NOP
     0160    B651              LDA    CUR      ;GET CURRENT LATCH CODE
     0162    B701              STA    PDRB     ;LATCH CLOCK PULSE UP
     0164    9D                NOP
     0165    A600              LDA    #00
     0167    B701              STA    PDRB     ;LATCH CLOCK PULSE DOWN
```

UNITED STATES PATENT AND TRADEMARK OFFICE
CERTIFICATE OF CORRECTION

PATENT NO. : 5,041,973
DATED : August 20, 1991
INVENTOR(S) : Lebron et al.

It is certified that error appears in the above-identified patent and that said Letters Patent is hereby corrected as shown below:

```
0169   A600            LDA    #00
016B   B702            STA    PDRC   ;ENABLE LATCHES
016D   A666            LDA    #PUTM
016F   CD045A          JSR    DLOOP       ;PULSE UP TIME
0172   A601            LDA    #01
0174   B702            STA    PDRC   ;DISIBLE LATCHES
0176   A600            LDA    #00
0178   B700            STA    PDRA   ;DATA OUT LINES = 00000000
017A   9D              NOP
0178   B651            LDA    CUR    ;GET CURRENT LATCH CODE
017D   B701            STA    PDRB   ;LATCH CLOCK PULSE UP
017F   9D              NOP
0180   A600            LDA    #00
0182   B701            STA    PDRB   ;LATCH CLOCK PULSE DOWN
0184   B651            LDA    CUR
0186   4C              INCA
0187   B751            STA    CUR    ;NEXT LATCH
0189   B650            LDA    TEMP
018B   A001            SUB    #01
018D   2709            BEQ    M3OUT       ;BRANCH IF ALL 7 LATCHES DONE
018F   B750            STA    TEMP
0191   AEOA            LDX    #010
0193   CD0462          JSR    D1LOOP      ;10mS IN BETWEEN PULSES
0196   20C3            BRA    M3LOOP      ;NEXT LATCH
0198   81       M3OUT  RTS
0199                   ;********************MAP 4 STAR SCAN (SQUARE), FIXED
0199   BDFB     MAP4   JSR    CLEAR
019B   A601            LDA    #01
019D   B702            STA    PDRC   ;DISABLE LATCHES
                       ;-----------------------------------------------------
019F   A618            LDA    #018H
01A1   B700            STA    PDRA   ;FIRST DATA GROUP
01A3   A604            LDA    #04
01A5   CD0450          JSR    LATCH       ;GOES TO LATCH 4
01A8   CD0435          JSR    SQU    ;OUTPUT FIRST SQUARE
```

UNITED STATES PATENT AND TRADEMARK OFFICE
CERTIFICATE OF CORRECTION

PATENT NO. : 5,041,973

DATED : August 20, 1991

INVENTOR(S) : Lebron et al.

It is certified that error appears in the above-identified patent and that said Letters Patent is hereby corrected as shown below:

```
                    ;------------------------------------------
    01AB    A63C        LDA    #03CH
    01AD    B700        STA    PDRA  ;SECOND DATA GROUP
    01AF    A603        LDA    #03
    01B1    CD0450      JSR    LATCH       ;GOES TO LATCH 3
    01B4    A605        LDA    #05
    01B6    CD0450      JSR    LATCH       ;GOES TO LATCH 5
    01B9    A624        LDA    #024H
    01BB    B700        STA    PDRA  ;SECOND DATA GROUP
    01BD    A604        LDA    #04
    01BF    CD0450      JSR    LATCH       ;GOES TO LATCH 4--
```

Delete columns 17 and 18 in their entirety and substitute the following therefore:

```
  --01C2    CD0435      JSR    SQU   ;OUTPUT SECOND SQUARE
                    ;------------------------------------------
    01C5    A67E        LDA    #07EH
    01C7    B700        STA    PDRA  ;THIRD DATA GROUP
    01C9    A602        LDA    #02
    01CB    CD0450      JSR    LATCH       ;GOES TO LATCH 2
    01CE    A606        LDA    #06
    01D0    CD0450      JSR    LATCH       ;GOES TO LATCH 6
    01D3    A642        LDA    #042H
    01D5    B700        STA    PDRA  ;THIRD DATA GROUP
    01D7    A603        LDA    #03
    01D9    CD0450      JSR    LATCH       ;GOES TO LATCH 3
    01DC    A604        LDA    #04
    01DE    CD0450      JSR    LATCH       ;GOES TO LATCH 4
    01E1    A605        LDA    #05
    01E3    CD0450      JSR    LATCH       ;GOES TO LATCH 5
    01E6    CD0435      JSR    SQU   ;OUTPUT THIRD SQUARE
                    ;------------------------------------------
    01E9    A6FF        LDA    #0FFH
    01EB    B700        STA    PDRA  ;FOURTH DATA GROUP
    01ED    A601        LDA    #01
    01EF    CD0450      JSR    LATCH       ;GOES TO LATCH 1
```

UNITED STATES PATENT AND TRADEMARK OFFICE
CERTIFICATE OF CORRECTION

PATENT NO. : 5,041,973

DATED : August 20, 1991

INVENTOR(S) : Lebron et al.

It is certified that error appears in the above-identified patent and that said Letters Patent is hereby corrected as shown below:

```
     01F2    A607            LDA    #07
     01F4    CD0450          JSR    LATCH      ;GOES TO LATCH 7
     01F7    A681            LDA    #081H
     01F9    B700            STA    PDRA  ;FOURTH DATA GROUP
     01FB    A602            LDA    #02
     01FD    CD0450          JSR    LATCH      ;GOES TO LATCH 2
     0200    A603            LDA    #03
     0202    CD0450          JSR    LATCH      ;GOES TO LATCH 3
     0205    A604            LDA    #04
     0207    CD0450          JSR    LATCH      ;GOES TO LATCH 4
     020A    A605            LDA    #05
     020C    CD0450          JSR    LATCH      ;GOES TO LATCH 5
     020F    A606            LDA    #06
     0211    CD0450          JSR    LATCH      ;GOES TO LATCH 6
     0214    CD0435          JSR    SQU   ;OUTPUT FOURTH SQUARE
                             ;---------------------------------------
     0217    81              RTS

;****************MAP 5 HORIZONTAL SCAN EXPONENTIA
                             G

0218    A600      MAP5  LDA    #00
     021A    B701            STA    PDRB
     021C    A680            LDA    #080H      ;THE INITIAL INBETWEEN TIME
     021E    B750            STA    TEMP  ;SAVE IT
     0220    A601            LDA    #01   ;THE INITIAL LATCH DATA
     0222    B751            STA    CUR   ;SAVE IT
     0224    B700      M5LOOP       STA    PDRA  ;LATCH DATA TO PORT A
     0226    BDFF            JSR    NOCLR      ;SAVE IT TO THE LATCHES
     0228    A600            LDA    #00--
```

Delete columns 19 and 20 in their entirety and substitute the following therefore:

```
  --022A    B701            STA    PDRB
    022C    B702            STA    PDRC  ;ENABLE LATCH OUTPUTS
    022E    A666            LDA    #PUTM      ;GET PULSE UP TIME
```

UNITED STATES PATENT AND TRADEMARK OFFICE
CERTIFICATE OF CORRECTION

PATENT NO. : 5,041,973

DATED : August 20, 1991

INVENTOR(S) : Lebron et al.

It is certified that error appears in the above-identified patent and that said Letters Patent is hereby corrected as shown below:

```
0230    CD045A              JSR    DLOOP      ;DELAY
0233    A601                LDA    #01
0235    B702                STA    PDRC       ;DISALE LATCH OUTPUTS
0237    BE50                LDX    TEMP       ;GET EXP DELAY TIME
0239    CD0458      EXLOOP  JSR    D1MS       ;DELAY FOR 1MS
023C    5A                  DEX               ;DECREMENT X COUNTER
023D    26FA                BNE    EXLOOP     ;BRANCH IF DELAY NOT DONE
023F    B650                LDA    TEMP
0241    44                  LSRA              ;NEXT DELAY TIME
0242    2502                BCS    GOUT       ;BRANCH IF ALL 8 DONE
0244    2001                BRA    GO
0246    81          GOUT    RTS
0247    B750        GO      STA    TEMP       ;SAVE NEW DELAY TIME
0249    B651                LDA    CUR        ;GET CURRENT LATCH DATA
024B    48                  ASLA              ;NEXT LATCH DATA
024C    B751                STA    CUR        ;SAVE IT
024E    CC0224              JMP    M5LOOP     ;NEXT PULSE

;*****************MAP 6 (ALL CHANNELS 5mS APPART)
0251    A607        MAP6    LDA    #07
0253    B750                STA    TEMP       ;7 LATCHES TO DO
0255    A601                LDA    #01
0257    B751                STA    CUR        ;THE CURRENT LATCH
0259    A601                LDA    #01
025B    B752                STA    TMP        ;CURRENT DATA OUTPUT
025D    B652        LP6     LDA    TMP
025F    B700                STA    PDRA       ;OUTPUT DATA
0261    9D                  NOP
0262    B651                LDA    CUR
0264    B701                STA    PDRB       ;CURRENT LATCH CODE
0266    9D                  NOP
0267    A600                LDA    #00
0269    B701                STA    PDRB       ;LATCH PULSE DOWN
026B    A600                LDA    #00
026D    B702                STA    PDRC       ;ENABLE LATCHES
026F    A666                LDA    #PUTM
0271    CD045A              JSR    DLOOP      ;PULSE UP TIME
```

UNITED STATES PATENT AND TRADEMARK OFFICE
CERTIFICATE OF CORRECTION

PATENT NO.   :   5,041,973

DATED        :   August 20, 1991

INVENTOR(S)  :   Lebron et al.

It is certified that error appears in the above-identified patent and that said Letters Patent is hereby corrected as shown below:

```
     0274    A601              LDA   #01
     0276    B702              STA   PDRC   ;DISABLE LATCHES
     0278    BDFB              JSR   CLEAR
     027A    AE0A              LDX   #010
     027C    CD0462            JSR   D1LOOP; 10 mS DELAY BETWEEN PULSES
     027F    B652              LDA   TMP
     0281    48                ASLA
     0282    2505              BCS   SMGO   ;BRANCH IF ALL 8 LINES DONE
     0284    B752              STA   TMP    ;SAVE CURRENT DATA
     0286    CC025D            JMP   LP6    ;LOOP TO NEXT DATA
     0289    BDFB      SMGO    JSR   CLEAR
     028B    B650              LDA   TEMP
     028D    A001              SUB   #01
     028F    270E              BEQ   M6DN
     0291    B750              STA   TEMP--
```

Delete columns 21 and 22 in their entirety and substitute the following therefore:

```
   --0293    B651              LDA   CUR
     0295    4C                INCA         ;NEXT LATCH
     0296    B751              STA   CUR
     0298    A601              LDA   #01
     029A    B752              STA   TMP
     029C    CC025D            JMP   LP6    ;LOOP
     029F    81        M6DN    RTS
     02A0
     02A0
                               ;***************************MAP 7 "DL"

02A0    BDFB      MAP7    JSR   CLEAR
     02A2    A601              LDA   #01
     02A4    B702              STA   PDRC   ;DISABLE LATCHES
     02A6    A600              LDA   #00H
     02A8    B700              STA   PDRA
     02AA    A601              LDA   #01
     02AC    CD0450            JSR   LATCH;00H TO LATCH #1
```

UNITED STATES PATENT AND TRADEMARK OFFICE
CERTIFICATE OF CORRECTION

PATENT NO. : 5,041,973

DATED : August 20, 1991

INVENTOR(S) : Lebron et al.

It is certified that error appears in the above-identified patent and that said Letters Patent is hereby corrected as shown below:

```
02AF    A607        LDA   #07
02B1    CD0450      JSR   LATCH;00H TO LATCH #7
02B4    A626        LDA   #026H
02B6    B700        STA   PDRA
02B8    A602        LDA   #02
02BA    CD0450      JSR   LATCH;26H TO LATCH #2
02BD    A62A        LDA   #02AH
02BF    B700        STA   PDRA
02C1    A603        LDA   #03
02C3    CD0450      JSR   LATCH;2AH TO LATCH #3
02C6    A604        LDA   #04
02C8    CD0450      JSR   LATCH;2AH TO LATCH #4
02CB    A605        LDA   #05
02CD    CD0450      JSR   LATCH;2AH TO LATCH #5
02D0    A666        LDA   #066H
02D2    B700        STA   PDRA
02D4    A606        LDA   #06
02D6    CD0450      JSR   LATCH;66H TO LATCH #6
02D9    CD0435      JSR   SQU   ;OUTPUT FIRST PULSES
02DC    A6FF        LDA   #0FFH
02DE    B700        STA   PDRA
02E0    A601        LDA   #01
02E2    CD0450      JSR   LATCH;FFH TO LATCH #1
02E5    A607        LDA   #07
02E7    CD0450      JSR   LATCH;FFH TO LATCH #7
02EA    A6D9        LDA   #0D9H
02EC    B700        STA   PDRA
02EE    A602        LDA   #02
02F0    CD0450      JSR   LATCH;D9H TO LATCH #2
02F3    A6D5        LDA   #0D5H
02F5    B700        STA   PDRA
02F7    A603        LDA   #03
02F9    CD0450      JSR   LATCH;D5H TO LATCH #3
02FC    A604        LDA   #04
02FE    CD0450      JSR   LATCH;D5H TO LATCH #4
```

UNITED STATES PATENT AND TRADEMARK OFFICE
CERTIFICATE OF CORRECTION

PATENT NO. : 5,041,973

DATED : August 20, 1991

INVENTOR(S) : Lebron et al.

It is certified that error appears in the above-identified patent and that said Letters Patent is hereby corrected as shown below:

```
     0301    A605           LDA   #05
     0303    CD0450         JSR   LATCH;D5H TO LATCH #5--
```

Delete columns 23 and 24 in their entirety and substitute the following therefore:

```
--0306    A699           LDA   #099H
  0308    B700           STA   PDRA
  030A    A606           LDA   #06
  030C    CD0450         JSR   LATCH;99H TO LATCH #6
  030F    CD0435         JSR   SQU   ;OUTPUT SECOND PULSES
  0312    81             RTS
  0313

;*****************************MAP 8 (CHECKER BOARD)

0313    BDFB    MAP8   JSR   CLEAR
  0315    A655           LDA   #055H
  0317    B700           STA   PDRA
  0319    A601           LDA   #01
  031B    CD0450         JSR   LATCH;55H TO LATCH #1
  031E    A603           LDA   #03
  0320    CD0450         JSR   LATCH;55H TO LATCH #3
  0323    A605           LDA   #05
  0325    CD0450         JSR   LATCH;55H TO LATCH #5
  0328    A607           LDA   #07
  032A    CD0450         JSR   LATCH;55H TO LATCH #7
  032D    A6AA           LDA   #0AAH
  032F    B700           STA   PDRA
  0331    A602           LDA   #02
  0333    CD0450         JSR   LATCH;AAH TO LATCH #2
  0336    A604           LDA   #04
  0338    CD0450         JSR   LATCH;AAH TO LATCH #4
  033B    A606           LDA   #06
  033D    CD0450         JSR   LATCH;AAH TO LATCH #6
  0340    CD0435         JSR   SQU   ;OUTPUT FIRST PULSES
  0343    A6AA           LDA   #0AAH
```

UNITED STATES PATENT AND TRADEMARK OFFICE
CERTIFICATE OF CORRECTION

PATENT NO. : 5,041,973

DATED : August 20, 1991

INVENTOR(S) : Lebron et al.

It is certified that error appears in the above-identified patent and that said Letters Patent is hereby corrected as shown below:

```
    0345    B700            STA   PDRA
    0347    A601            LDA   #01
    0349    CD0450          JSR   LATCH;AAH TO LATCH #1
    034C    A603            LDA   #03
    034E    CD0450          JSR   LATCH;AAH TO LATCH #3
    0351    A605            LDA   #05
    0353    CD0450          JSR   LATCH;AAH TO LATCH #5
    0356    A607            LDA   #07
    0358    CD0450          JSR   LATCH;AAH TO LATCH #7
    035B    A655            LDA   #055H
    035D    B700            STA   PDRA
    035F    A602            LDA   #02
    0361    CD0450          JSR   LATCH;55H TO LATCH #2
    0364    A604            LDA   #04
    0366    CD0450          JSR   LATCH;55H TO LATCH #4
    0369    A606            LDA   #06
    036B    CD0450          JSR   LATCH;55H TO LATCH #6
    036E    CD0435          JSR   SQU   ;OUTPUT SECOND PULSES
    0371    81              RTS

;*****************************MAP 9 (CROSS PATTERN)

0372    BDFB    MAP9 JSR  CLEAR
    0374    A618         LDA  #018H--
```

Delete columns 25 and 26 in their entirety and substitute the following therefore:

```
  --0376    B700            STA   PDRA
    0378    A601            LDA   #01
    037A    CD0450          JSR   LATCH;18H TO LATCH #1
    037D    A602            LDA   #02
    037F    CD0450          JSR   LATCH;18H TO LATCH #2
    0382    A603            LDA   #03
    0384    CD0450          JSR   LATCH;18H TO LATCH #3
    0387    A605            LDA   #05
    0389    CD0450          JSR   LATCH;18H TO LATCH #5
```

UNITED STATES PATENT AND TRADEMARK OFFICE
CERTIFICATE OF CORRECTION

PATENT NO. : 5,041,973

DATED : August 20, 1991

INVENTOR(S) : Lebron et al.

It is certified that error appears in the above-identified patent and that said Letters Patent is hereby corrected as shown below:

```
038C    A606        LDA   #06
038E    CD0450      JSR   LATCH;18H TO LATCH #6
0391    A607        LDA   #07
0393    CD0450      JSR   LATCH;18H TO LATCH #7
0396    A6FF        LDA   #0FFH
0398    B700        STA   PDRA
039A    A604        LDA   #04
039C    CD0450      JSR   LATCH;FFH TO LATCH #4
039F    CD0435      JSR   SQU  ;OUTPUT FIRST PULSES
03A2    A624        LDA   #024H
03A4    B700        STA   PDRA
03A6    A601        LDA   #01
03A8    CD0450      JSR   LATCH;24H TO LATCH #1
03AB    A602        LDA   #02
03AD    CD0450      JSR   LATCH;24H TO LATCH #2
03B0    A606        LDA   #06
03B2    CD0450      JSR   LATCH;24H TO LATCH #6
03B5    A607        LDA   #07
03B7    CD0450      JSR   LATCH;24H TO LATCH #7
03BA    A6E7        LDA   #0E7H
03BC    B700        STA   PDRA
03BE    A603        LDA   #03
03C0    CD0450      JSR   LATCH;E7H TO LATCH #3
03C3    A605        LDA   #05
03C5    CD0450      JSR   LATCH;E7H TO LATCH #5
03C8    A600        LDA   #00H
03CA    B700        STA   PDRA
03CC    A604        LDA   #04
03CE    CD0450      JSR   LATCH;00H TO LATCH #4
03D1    CD0435      JSR   SQU  ;OUTPUT SECOND PULSES
03D4    A642        LDA   #042H
03D6    B700        STA   PDRA
03D8    A601        LDA   #01
03DA    CD0450      JSR   LATCH;42H TO LATCH #1
03DD    A607        LDA   #07
03DF    CD0450      JSR   LATCH;42H TO LATCH #7
03E2    A6C3        LDA   #0C3H
```

UNITED STATES PATENT AND TRADEMARK OFFICE
CERTIFICATE OF CORRECTION

PATENT NO. : 5,041,973
DATED : August 20, 1991
INVENTOR(S) : Lebron et al.

It is certified that error appears in the above-identified patent and that said Letters Patent is hereby corrected as shown below:

```
03E4    B700         STA  PDRA
03E6    A602         LDA  #02
03E8    CD0450       JSR  LATCH;C3H TO LATCH #2
03EB    A606         LDA  #06
03ED    CD0450       JSR  LATCH;C3H TO LATCH #6
03F0    A600         LDA  #00H
03F2    B700         STA  PDRA
03F4    A603         LDA  #03
03F6    CD0450       JSR  LATCH;00H TO LATCH #3
03F9    A604         LDA  #04--
```

Delete columns 27 and 28 in their entirety and substitute the following therefore:

```
--03FB  CD0450       JSR  LATCH;00H TO LATCH #4
03FE    A605         LDA  #05
0400    CD0450       JSR  LATCH;00H TO LATCH #5
0403    CD0435       JSR  SQU    ;OUTPUT THIRD PULSES
0406    A681         LDA  #81H
0408    B700         STA  PDRA
040A    A601         LDA  #01
040C    CD0450       JSR  LATCH;81H TO LATCH #1
040F    A607         LDA  #07
0411    CD0450       JSR  LATCH;81H TO LATCH #7
0414    A600         LDA  #00H
0416    B700         STA  PDRA
0418    A602         LDA  #02
041A    CD0450       JSR  LATCH;00H TO LATCH #2
041D    A603         LDA  #03
041F    CD0450       JSR  LATCH;00H TO LATCH #3
0422    A604         LDA  #04
0424    CD0450       JSR  LATCH;00H TO LATCH #4
0427    A605         LDA  #05
0429    CD0450       JSR  LATCH;00H TO LATCH #5
042C    A606         LDA  #06
042E    CD0450       JSR  LATCH;00H TO LATCH #6
```

UNITED STATES PATENT AND TRADEMARK OFFICE
CERTIFICATE OF CORRECTION

PATENT NO. : 5,041,973

DATED : August 20, 1991

INVENTOR(S) : Lebron et al.

It is certified that error appears in the above-identified patent and that said Letters Patent is hereby corrected as shown below:

```
0431    CD0435            JSR   SQU    ;OUTPUT FOURTH PULSES
0434    81                RTS

;************************OUTPUT SQUARE SUBROUTINE

0435    A600      SQU     LDA   #00
0437    B700              STA   PDRA   ;DATA GROUP OFF
0439    B702              STA   PDRC   ;SQUARE ENABLED
043B    A666              LDA   #PUTM
043D    CD045A            JSR   DLOOP         ;SQUARE ON TIME
0440    A601              LDA   #01
0442    B702              STA   PDRC   ;SQUARE DISABLED
0444    BDFB              JSR   CLEAR         ;CLEAR THE LATCHES
0446    A600              LDA   #00
0448    B701              STA   PDRB
044A    AEOA              LDX   #010
044C    CD0462            JSR   D1LOOP        ;10 mS DELAY BETWEEN PULSES
044F    81                RTS

0450
                          ;*********************************LATCH SUBROUTINE

0450    B701      LATCH   STA   PDRA   ;LATCH PULSE UP
0452    9D                NOP
0453    A600              LDA   #00
0455    B701              STA   PDRB   ;LATCH PULSE DOWN
0457    81                RTS
0458
0458
                          ;******************1MS DELAY SUBROUTINE (DESTROYS T

0458    A629      D1MS LDA    #41    ;DECIMAL 41 IS THE 1MS COUNT
045A    4A        DLOOP      DECA--
```

Delete columns 29 and 30 in their entirety and substitute the following therefore:

UNITED STATES PATENT AND TRADEMARK OFFICE
CERTIFICATE OF CORRECTION

PATENT NO. : 5,041,973

DATED : August 20, 1991

INVENTOR(S) : Lebron et al.

It is certified that error appears in the above-identified patent and that said Letters Patent is hereby corrected as shown below:

```
--045B   2702             BEQ   DDONE     ;BRANCH IF DONE
  045D   20FB             BRA   DLOOP     ;LOOP
  045F   81       DDONE   RTS             ;RETURN FROM SUBROUTINE

;*****************100MS DELAY SUBROUTINE (DESTROYS
                  ' & X')

0460   AE64   D100MS   LDX   #100       ;DECIMAL 100
  0462   5A     D1LOOP   DECX
  0463   2705            BEQ   D10UT      ;BRANCH IF DONE
  0465   CD0458          JSR   D1MS       ;DELAY 1MS
  0468   20F8            BRA   D1LOOP
  046A   81     D10UT    RTS

;******************WAIT SUBROUTINE (.5 SECOND DELAY)

046B   A605   WAIT     LDA   #05H
  046D   B750   WLOOP    STA   TEMP
  046F   CD0460          JSR   D100MS     ;DELAY 100MS
  0472   B650            LDA   TEMP
  0474   4A              DECA
  0475   26F6            BNE   WLOOP      ;BRANCH IF NOT DONE 1S
  0477   81              RTS
  0478

;***********************INTERRUPT VECTORS

OFF8                   ORG   OFF8H
  OFF8   0080            DW    0080H
  OFFA   0080            DW    0080H
  OFFC   0080            DW    0080H
  OFFE   0080            DW    0080H

0080                   END   0080H
```

UNITED STATES PATENT AND TRADEMARK OFFICE
CERTIFICATE OF CORRECTION

PATENT NO. : 5,041,973
DATED : August 20, 1991
INVENTOR(S) : Lebron et al.

It is certified that error appears in the above-identified patent and that said Letters Patent is hereby corrected as shown below:

```
---- SYMBOL TABLE ----

ACR      000E        LATCH    0450        NOCLR    00FF
APR      000F        LP6      025D        OUT1     009D
CLEAR    00FB        M2DONE   0150        PCR      000B
CLLOOP   0101        M2LOOP   0130        PDRA     0000
CLOUT    010D        M3LOOP   015B        PDRB     0001
CUR      0051        M3OUT    0198        PDRC     0002
D100MS   0460        M5LOOP   0224        PDRD     0003
D1LOOP   0462        M6DN     029F        PUTM     0066
D1MS     0458        MAP1     0112        SMGO     0289
D1OUT    046A        MAP2     0126        SQU      0435
DDONE    045F        MAP3     0151        TCR      0009
DDRA     0004        MAP4     0199        TDR      0008
DDRB     0005        MAP5     0218        TEMP     0050
DDRC     0006        MAP6     0251        TEST     0089
DLOOP    045A        MAP7     02A0        TMP      0052
END      00F5        MAP8     0313        WAIT     046B
EXLOOP   0239        MAP9     0372        WLOOP    046D--
GO       0247        MOR      0F38
GOUT     0246        MR       000A
```

Signed and Sealed this

Nineteenth Day of April, 1994

BRUCE LEHMAN

Attesting Officer      Commissioner of Patents and Trademarks